United States Patent
Genet et al.

(10) Patent No.: US 6,402,791 B1
(45) Date of Patent: Jun. 11, 2002

(54) CATIONIC DI-METHYLENEDIOXY-BENZENES, THEIR USE FOR OXIDATION DYEING OF KERATIN FIBRES

(75) Inventors: Alain Genet, Aulnay-sous-Bois; Alain Lagrange, Coupvray, both of (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/646,643

(22) PCT Filed: Jan. 14, 2000

(86) PCT No.: PCT/FR00/00075

§ 371 (c)(1),
(2), (4) Date: Nov. 21, 2000

(87) PCT Pub. No.: WO00/43389

PCT Pub. Date: Jul. 27, 2000

(30) Foreign Application Priority Data

Jan. 21, 1999 (FR) .............................. 99 00636

(51) Int. Cl.$^7$ ............................................ A61K 7/13
(52) U.S. Cl. .................. 8/405; 8/406; 8/408; 8/409; 8/554; 8/570; 8/573; 549/437; 549/438
(58) Field of Search ................ 8/405, 406, 408, 8/409, 554, 570, 573; 549/437, 438

(56) References Cited

U.S. PATENT DOCUMENTS

| | | | |
|---|---|---|---|
| 4,003,699 A | 1/1977 | Rose et al. | 8/10.2 |
| 4,395,262 A | 7/1983 | Konrad et al. | 8/410 |
| 4,823,985 A | 4/1989 | Grollier et al. | 222/1 |
| 4,865,617 A | 9/1989 | Junino et al. | 8/409 |
| 5,061,289 A | 10/1991 | Clausen et al. | 8/405 |
| 5,380,340 A | 1/1995 | Neunhoeffer et al. | 8/409 |
| 5,766,576 A | 6/1998 | Löwe et al. | |

FOREIGN PATENT DOCUMENTS

| | | |
|---|---|---|
| DE | 23 59 399 | 6/1975 |
| DE | 37 29 493 | 3/1988 |
| DE | 38 43 892 | 6/1990 |
| DE | 41 33 957 | 4/1993 |
| DE | 195 43 988 | 5/1997 |
| EP | 0 008 080 | 2/1980 |
| FR | 2 586 913 | 3/1987 |
| FR | 2 733 749 | 11/1996 |
| FR | 2 750 048 | 12/1997 |
| GB | 1 153 196 | 5/1969 |
| GB | 1 026 978 | 4/1996 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

Co–pending Application No. 09/646,644; Attorney Docket No. 05725.0760–00000 Cationic Methylenedioxy Benzenes, Their Use for Oxidation Dyeing of Keratin Fibres, Dyeing Compositions and Methods Alain Genet et al. Nov. 21, 2000.
Chemical Abstracts, vol. 107, No. 20, 1987, Abstract No. 187436q, p. 774, col. 1.
English language Derwent Abstract of FR 2 733 749.
English language Derwent Abstract of FR 2 750 048.
English language Derwent Abstract of JP 2–19576.
English language Derwent Abstract of JP 9–110659.

*Primary Examiner*—Mark Kopec
*Assistant Examiner*—Eisa Elhilo
(74) *Attorney, Agent, or Firm*—Finnegan, Henderson, Farabow, Garrett & Dunner, L.L.P.

(57) ABSTRACT

The subject of the invention is novel dimethylenedioxybenzenes comprising at least one cationic group Z, Z being chosen from quaternized aliphatic chains, aliphatic chains comprising at least one quaternized saturated ring, and aliphatic chains comprising at least one quaternized unsaturated ring, their use as oxidation dye precursor for the oxidation dyeing of keratinous fibres, dyeing compositions containing them, as well as the oxidation dyeing methods using them.

31 Claims, No Drawings

CATIONIC DI-METHYLENEDIOXY-BENZENES, THEIR USE FOR OXIDATION DYEING OF KERATIN FIBRES

The subject of the invention is novel dimethylenedioxybenzenes comprising at least one cationic group Z, Z being chosen from quaternized aliphatic chains, aliphatic chains comprising at least one quaternized saturated ring, and aliphatic chains comprising at least one quaternized unsaturated ring, their use as oxidation dye precursor for the oxidation dyeing of keratinous fibres, dyeing compositions containing them, as well as the oxidation dyeing methods using them.

It is known to dye keratinous fibres, and in particular human hair, with dyeing compositions containing oxidation dye precursors, in particular para-phenylenediamines, ortho- or para-aminophenols, heterocyclic compounds such as diaminopyrazole derivatives, generally called oxidation bases. Oxidation dye precursors, or oxidation bases, are colourless or weakly coloured compounds which, combined with oxidizing products, can give rise, by a process of oxidative condensation, to coloured and colouring compounds.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds such as for example indolic couplers.

The variety of the molecules used in oxidation bases and couplers makes it possible to obtain a rich palette of colours.

The so-called "permanent" colour obtained using these oxidation dyes must moreover meet a number of requirements. Thus, it must be without drawbacks from the toxicological point of view, it must make it possible to obtain shades in the desired intensity and exhibit good resistance to external agents (light, adverse weather conditions, washing, permanent waving, perspiration, rubbing).

The dyes must also make it possible to cover grey hair, and be the least selective possible, that is to say make it possible to obtain the smallest possible differences in colour right along the same keratinous fibre, which may indeed be differently sensitized (i.e. damaged) between its tip and its root.

However, the Applicant has now just discovered, completely unexpectedly and surprisingly, that a novel family of dimethylenedioxybenzenes of formula (I) defined below, comprising at least one cationic group Z, Z being chosen from quaternized aliphatic chains, aliphatic chains comprising at least one quaternized saturated ring, and aliphatic chains comprising at least one quaternized unsaturated ring, is not only suitable for use as oxidation dye precursor for oxidation dyeing, but, in addition, that it makes it possible to obtain dyeing compositions leading to intense colours, in a very broad palette of shades and exhibiting excellent properties of resistance to different treatments to which the keratinous fibres may be subjected.

These discoveries form the basis of the present invention.

The first subject of the invention is therefore dimethylenedioxybenzenes of the following formula (I), and their addition salts with an acid:

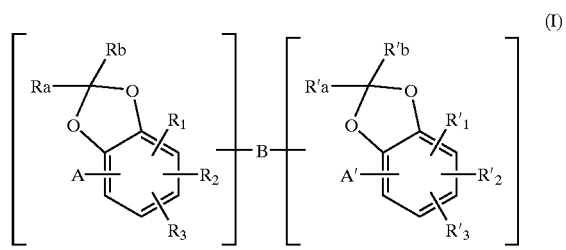

in which:

B is a linking arm which represents a linear or branched alkyl chain preferably comprising from 1 to 14 carbon atoms, which may be interrupted by one or more groups Z as defined below and/or by one or more heteroatoms such as oxygen, sulphur or nitrogen atoms, and optionally substituted with one or more hydroxyl or $C_1$–$C_6$ alkoxy radicals, and which may carry one or more ketone functions;

Ra, Rb, R'a and R'b, which are identical or different, may represent a hydrogen atom, a $C_1$–$C_6$ alkyl radical, a $C_1$–$C_6$ hydroxyalkyl radical, or form in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, represent a hydrogen atom; a halogen atom; one of the two valences of a linking arm B, a group Z as defined below; a group $A_2$ as defined below; a group $A_2'$ as defined below; a ($C_1$–$C_6$)alkylcarbonyl radical; an amino($C_1$–$C_6$)alkylcarbonyl radical; an N-Z-amino ($C_1$–$C_6$)alkylcarbonyl radical; an N-($C_1$–$C_6$) alkylamino($C_1$–$C_6$)alkylcarbonyl radical; an N,N-di ($C_1$–$C_6$ alkyl)amino($C_1$–$C_6$)alkylcarbonyl radical; an amino($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$ alkyl)amino($C_1$–$C_6$)alkylcarbonyl ($C_1$–$C_6$)alkyl radical; an N,N-di($C_1$–$C_6$ alkyl)amino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N-Z-aminosulphonyl radical; an N-($C_1$–$C_6$ alkyl) aminosulphonyl radical; an N,N-di($C_1$–$C_6$ alkyl) aminosulphonyl radical; an aminosulphonyl($C_1$–$C_6$) alkyl radical; an N-Z-aminosulphonyl($C_1$–$C_6$)alkyl radical; an N-($C_1$–$C_6$ alkyl)aminosulphonyl($C_1$–$C_6$) alkyl radical; an N,N-di($C_1$–$C_6$ alkyl)aminosulphonyl ($C_1$–$C_6$)alkyl radical; a carbamyl radical; an N-($C_1$–$C_6$ alkyl)carbamyl radical; an N,N-di($C_1$–$C_6$ alkyl) carbamyl radical; a carbamyl($C_1$–$C_6$)alkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$, $OR'_6$, $SR_6$ or $SR'_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two radicals, which are identical or different, chosen from the alkyl, $C_1$–$C_6$ monohydroxyalkyl, $C_2$–$C_6$ polyhydroxyalkyl, ($C_1$–$C_6$)

alkylcarbonyl, carbamyl, N-($C_1$–$C_6$ alkyl)carbamyl or N,N-di($C_1$–$C_6$ alkyl)carbamyl, $C_1$–$C_6$)alkylsulphonyl, formyl, trifluoro($C_1$–$C_6$)alkylcarbonyl, ($C_1$–$C_6$) alkylcarboxyl or thiocarbamyl radicals, or from the groups Z as defined below, or which can form together, with the nitrogen atom to which they are attached, a 5- or 6-membered ring, containing carbon or containing one or more heteroatoms;

$R_6$ and $R'_6$, which may be identical or different, denote one of the two valences of a linking arm B; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a $C_1$–$C_6$ carboxyalkyl radical; a ($C_1$–$C_6$)alkylcarboxy($C_1$–$C_6$)alkyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$ alkyl)aminosulphonyl($C_1$–$C_6$)alkyl radical; an N,N-di($C_1$–$C_6$ alkyl)aminosulphonyl ($C_1$–$C_6$)alkyl radical; a ($C_1$–$C_6$)alkylsulphonyl($C_1$–$C_6$) alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an amino($C_1$–$C_6$)alkyl radical; an amino($C_1$–$C_6$)alkyl radical in which the alkyl is unsubstituted or substituted with one or more hydroxyl radicals and in which the amine is substituted with one or two radicals, which are identical or different, chosen from the ($C_1$–$C_6$) alkylmonohydroxy($C_1$–$C_6$)alkyl, polyhydroxy($C_2$–$C_6$) alkyl, ($C_1$–$C_6$)alkylcarbonyl, formyl, trifluoro($C_1$–$C_6$) alkylcarbonyl, ($C_1$–$C_6$)alkylcarboxyl, carbamyl, N-($C_1$–$C_6$ alkyl)carbamyl, N,N-di($C_1$–$C_6$ alkyl) carbamyl, thiocarbamyl and ($C_1$–$C_6$)alkylsulphonyl radicals, and among the groups Z as defined below; or which can form, together with the nitrogen atom to which they are attached, a 5- or 6-membered ring containing carbon or containing one or more heteroatoms;

$A_1$ represents a group —$NR_4R_5$ or a hydroxyl radical;

$A'_1$ represents a group —$NR'_4R'_5$ or a hydroxyl radical;

$A_2$ represents a group —$NR''_4R''_5$ or a hydroxyl radical;

$A'_2$ represents a group —$NR'''_4R'''_5$ or a hydroxyl radical;

$R_4$, $R_5$, $R'_4$, $R'_5$, $R''_4$, $R''_5$, $R'''_4$ and $R'''_5$, which are identical or different, represent one of the two valences of a linking arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ thiocarbamylalkyl radical; a $C_1$–$C_6$ trifluoroalkyl radical; a $C_1$–$C_6$ sulphoalkyl radical; a ($C_1$–$C_6$)alkylcarboxy($C_1$–$C_6$) alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from the $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N-($C_1$–$C_6$ alkyl)carbamyl, N,N-di($C_1$–$C_6$ alkyl)carbamyl, ($C_1$–$C_6$)alkylsulphonyl, formyl, trifluoro($C_1$–$C_6$ alkyl)carbonyl, ($C_1$–$C_6$)alkylcarboxyl and thiocarbamyl radicals, or from the groups Z as defined below, or which can form, together with the nitrogen atom to which they are attached, a 5- or 6-membered ring containing carbon or containing one or more heteroatoms;

Z is chosen from the unsaturated cationic groups of the following formulae (II) and (III), and the saturated cationic groups of the following formula (IV):

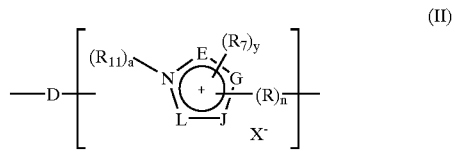

(II)

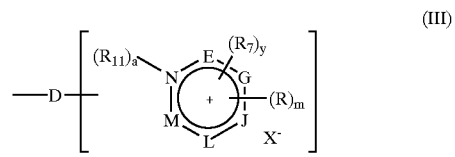

(III)

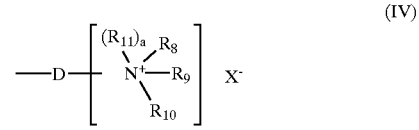

(IV)

in which

D is a linking arm which represents a linear or branched alkyl chain preferably comprising from 1 to 14 carbon atoms, which may be interrupted by one or more heteroatoms such as oxygen, sulphur or nitrogen atoms, and which may be substituted with one or more hydroxyl or $C_1$–$C_6$ alkoxy radicals, and which may carry one or more ketone functions;

the members E, G, J, L and M, which are identical or different, represent a carbon, oxygen, sulphur or nitrogen atom;

n is an integer between 0 and 4 inclusive;

m is an integer between 0 and 5 inclusive;

the radicals R, which are identical or different, represent one of the two valences of a linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a tri($C_1$–$C_6$ alkyl)silane ($C_1$–$C_6$)alkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$)alkylthio radical; an amino radical; an amino radical protected with a ($C_1$–$C_6$)alkylcarbonyl, carbamyl or ($C_1$–$C_6$)alkylsulphonyl radical; a group NHR'' or NR''R''' in which R'' and R''', which are identical or different, represent a $C_1$–$C_6$ alkyl radical, a $C_1$–$C_6$ monohydroxyalkyl radical or a $C_2$–$C_6$ polyhydroxyalkyl radical;

$R_7$ represents a $C_1$–$C_6$ alkyl radical; one of the two valences of a linking arm B; a $C_1$–$C_6$ monohydroxyalkyl radical; a $C_2$–$C_6$ polyhydroxyalkyl radical; a $C_1$–$C_6$ cyanoalkyl radical; a tri($C_1$–$C_6$ alkyl)silane ($C_1$–$C_6$)alkyl radical; a ($C_1$–$C_6$)alkoxy($C_1$–$C_6$)alkyl radical; a $C_1$–$C_6$ carbamylalkyl radical; a ($C_1$–$C_6$) alkylcarboxy($C_1$–$C_6$)alkyl radical; a benzyl radical; or a second group Z which is identical or different from the first group Z;

$R_8$, $R_9$ and $R_{10}$ which are identical or different, represent one of the two valences of a linking arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ cyanoalkyl radical; an aryl radical; a benzyl radical; a $C_1$–$C_6$ amidoalkyl radical; a tri($C_1$–$C_6$ alkyl)silane ($C_1$–$C_6$)alkyl radical; or a $C_1$–$C_6$ aminoalkyl radical in which the amine is protected by a ($C_1$–$C_6$) alkylcarbonyl, carbamyl or ($C_1$–$C_6$)alkylsulphonyl radical; two of the radicals $R_8$, $R_9$ and $R_{10}$ may also form together, with the nitrogen atom to which they are attached, a 5- or 6-membered saturated ring containing carbon or containing one or more heteroatoms such as for example a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri ($C_1$–$C_6$ alkyl)silane($C_1$–$C_6$)alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$)alkylthio radical, an amino radical, an amino radical protected by a ($C_1$–$C_6$)alkylcarbonyl, carbamyl or ($C_1$–$C_6$) alkylsulphonyl radical;

one of the radicals $R_8$, $R_9$ and $R_{10}$ can also represent a second group Z which is identical to or different from the first group Z;

$R_{11}$ represents one of the two valences of a linking arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or ($C_1$–$C_6$)alkylsulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silane($C_1$–$C_6$)alkyl radical; a $C_1$–$C_6$ sulphonamidoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$ alkyl) carbamyl($C_1$–$C_6$)alkyl radical; an N-($C_1$–$C_6$ alkyl) sulphonamido($C_1$–$C_6$)alkyl radical;

a and y are integers equal to 0 or 1; with the following conditions:
in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively 2) when at least one of the members E, G, J and L represents a nitrogen atom to which the radical $R_7$ is attached;
in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;
in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring;
$X^-$ represents a monovalent or divalent anion and is preferably chosen from a halogen atom such as chlorine, bromine, fluorine or iodine, a hydroxide, a hydrogen sulphate or a ($C_1$–$C_6$)alkyl sulphate such as for example a methyl sulphate or an ethyl sulphate;

it being understood that:
the number of cationic groups Z is at least equal to 1.

As indicated above, the colours obtained with the oxidation dyeing composition containing one or more compounds of formula (I) in accordance with the invention are intense and make it possible to obtain shades in a very broad palette of colours. They exhibit, furthermore, excellent properties of resistance against the action of the various external agents (light, adverse weather conditions, washing, permanent waving, perspiration, rubbing). These properties are particularly remarkable in particular as regards the resistance of the colours obtained to the action of light, washing and perspiration.

In formulae (I), (II), (III) and (IV) above, the alkyl and alkoxy radicals may be linear or branched.

Among the carbon-containing rings which can be formed conjointly by the radicals Ra and Rb or R'a and R'b, there may be particularly mentioned the pentane, hexane and heptane rings.

Among the rings of the unsaturated groups Z of formula (II) above, there may be mentioned in particular, by way of example, the pyrrole, imidazole, pyrazole, oxazole, thiazole and triazole rings.

Among the rings of the unsaturated groups Z of formula (III) above, there may be mentioned in particular, by way of example, the pyridine, pyrimidine, pyrazine, oxazine and triazine rings.

The compounds of formula (I) above are preferably chosen from:
3-[2-(6-aminobenzo[1,3]dioxol-5-ylamino)ethyl]-1-(4-{3-[2-(6-aminobenzo[1,3]dioxol-5-ylamino)ethyl]-3H-imidazol-1-ium}butyl)-3H-imidazol-1-ium dichloride;
3-[2-(6-hydroxybenzo[1,3]dioxol-5-ylamino)ethyl]-1-(4-{3-[2-(6-hydroxybenzo[1,3]dioxol-5-ylamino)ethyl]-3H-imidazol-1-ium}butyl)-3H-imidazol-1-ium dichloride;
3-[2-(6-methoxybenzo[1,3]dioxol-5-ylamino)ethyl]-1-(4-{3-[2-(6-methoxybenzo[1,3]dioxol-5-ylamino)ethyl]-3H-imidazol-1-ium}butyl)-3H-imidazol-1-ium dichloride;

1,3-bis[3-(6-aminobenzo[1,3]dioxol-5-yloxy)propyl]-3H-imidazol-1-ium chloride;

3-[2-(6-aminobenzo[1,3]dioxol-5-yloxy)ethyl]-1-(4-{3-[2-(6-aminobenzo[1,3]dioxol-5-yloxy)ethyl]-3H-imidazol-1-ium}butyl)-3H-imidazol-1-ium dichloride;

3-[3-(6-aminobenzo[1,3]dioxol-5-yloxy)propyl]-1-(4-{3-[3-(6-aminobenzo[1,3]dioxol-5-yloxy)propyl]-3H-imidazol-1-ium}butyl)-3H-imidazol-1-ium dichloride;

3-[2-(6-aminobenzo[1,3]dioxol-5-yloxy)ethyl]-1-(3-{[2-(6-aminobenzo[1,3]dioxol-5-yloxy)ethyl]dimethylammonium}propyl)-3H-imidazol-1-ium dichloride;

[2-(6-aminobenzo[1,3]dioxol-5-yloxy)ethyl]-(2-{[2-(6-aminobenzo[1,3]dioxol-5-yloxy)ethyl]dimethylammonium}ethyl)dimethylammonium dichloride;

and their addition salts with an acid.

The addition salts with an acid of the compounds of formula (I) in accordance with the invention are preferably chosen from hydrochlorides, hydrobromides, sulphates, citrates, succinates, tartrates, lactates and acetates.

The compounds of formula (I) in accordance with the invention can be easily obtained, according to methods well known in the state of the art, for example by reducing the corresponding cationic nitro compounds when these compounds contain an amino group.

This reducing step (production of a primary aromatic amine) followed or otherwise by salification, is in general, for convenience, the last step of the synthesis.

This reduction can take place earlier in the sequence of reactions leading to the preparation of the compounds of formula (I), and according to well known methods; it is then necessary to "protect" the primary amine created (for example by an acetylation, formylation or benzenesulphonation step, and the like), then carry out the desired substitutions or modifications (including the quaternization) and finish by the "deprotection" (in general in acid medium) of the amine function.

Likewise, the phenolic function may be protected according to well-known methods with a benzyl radical ("deprotection" by catalytic reduction) or with an acetyl or mesyl radical ("deprotection" in acid medium).

These cationic dimethylenedioxybenzene compounds are obtained by methods well known in the state of the art, for example by:

condensation of two molecules of a methylenedioxybenzene compound carrying a haloalkyl radical with one molecule of a compound carrying two tertiary amine radicals separated by a linking arm B as defined in the formula (I) described above, or alternatively, (a) condensation of one molecule of a methylenedioxybenzene compound carrying a tertiary amine radical with one molecule of a compound carrying two halogen radicals separated by a linking arm B as defined in the formula (I) described above, and (b) condensation of a second molecule of a methylenedioxybenzene compound different from the first and it too carrying a tertiary amine radical, or alternatively, (a) condensation of one molecule of a methylenedioxybenzene compound carrying a haloalkyl radical with one molecule of a compound carrying two tertiary amine radicals separated by a linking arm B as defined in the formula (I) described above, and (b) condensation of a second molecule of a methylenedioxybenzene compound different from the first and it too carrying a haloalkyl radical, or alternatively, condensation of one molecule of a methylenedioxybenzene compound carrying a tertiary amine radical with one molecule of a methylenedioxybenzene compound carrying a haloalkyl radical.

The haloalkyl radicals carried by the intermediate dimethylenedioxybenzene compounds can be prepared by known state of the art methods in one or more steps, for example by condensation of a dihaloalkyl compound with an amine or a hydroxyl, or by halogenation of a hydroxyalkyl chain.

When the synthesis is finished, the compounds of formula (I) in accordance with the invention can, where appropriate, be recovered by well known state of the art methods such as crystallization or distillation.

Another subject of the invention is the use of the compounds of formula (I) in accordance with the invention as oxidation dye precursor for the oxidation dyeing of keratinous fibres, and in particular human keratinous fibres such as hair.

The subject of the invention is also a composition for the oxidation dyeing of keratinous fibres and in particular human keratinous fibres such as hair, characterized in that it comprises, as oxidation dye precursor, in a medium appropriate for dyeing, at least one compound of formula (I) in accordance with the invention.

The compound(s) of formula (I) in accordance with the invention preferably represent from 0.0005 to 12% by weight approximately of the total weight of the dyeing composition, and still more preferably from 0.005 to 6% by weight approximately of this weight.

The medium appropriate for dyeing (or carrier) generally consists of water or of a mixture of water and of at least one organic solvent. As organic solvent, there may be mentioned for example lower $C_1$–$C_4$ alkanols, such as ethanol and isopropanol; glycerol, glycols and glycol ethers such as 2-butoxyethanol, propylene glycol, monomethyl ether of propylene glycol, monoethyl ether and monomethyl ether of diethylene glycol, as well as aromatic alcohols such as benzyl alcohol or phenoxyethanol, similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 3 and 12 approximately, and preferably between 5 and 11 approximately. It can be adjusted to the desired value by means of acidifying or alkalinizing agents normally used in dyeing keratinous fibres.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines as well as derivatives thereof, sodium or potassium hydroxides and the compounds of the following formula (V):

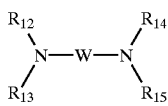

(V)

in which W is a propylene residue optionally substituted by an hydroxyl group or a $C_1$–$C_6$ alkyl radical; $R_{12}$, $R_{13}$, $R_{14}$ and $R_{15}$, which are identical or different, represent a hydrogen atom, a $C_1$–$C_6$ alkyl or $C_1$–$C_6$ hydroxyalkyl radical.

The dyeing composition in accordance with the invention may also contain, in addition to the compound(s) of formula (I) defined above, at least one oxidation base which may be chosen from the oxidation bases conventionally used in oxidation dyeing and among which there may be mentioned in particular para-phenylenediamines, bisphenylalkylenediamines, para-aminophenols, ortho-aminophenols and heterocyclic bases.

Among the para-phenylenediamines, there may be mentioned more particularly, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the bisphenylalkylenediamines, there may be mentioned more particularly, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, there may be mentioned more particularly, by way of example, para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

Among the ortho-aminophenols, there may be mentioned more particularly, by way of example, 2-aminophenol, 2-amino-5-methylphenol, 2-amino-6-methylphenol, 5-acetamido-2-aminophenol and their addition salts with an acid.

Among the heterocyclic bases, there may be mentioned more particularly, by way of example, the pyridine derivatives, the pyrimidine derivatives and the pyrazole derivatives.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or in Japanese Patents JP 88-169,571 and JP 91-10659 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]-pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)-amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, their tautomeric forms, when a tautomeric equilibrium exists, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE-195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

When they are used, these oxidation bases preferably represent from 0.0005 to 12% by weight approximately of the total weight of the dyeing composition, and still more preferably from 0.005 to 6% by weight approximately of this weight.

The oxidation dyeing compositions in accordance with the invention may also contain one or more couplers and/or one or more direct dyes, in particular for modifying the shades or enriching them with glints.

The couplers which can be used in the oxidation dyeing compositions in accordance with the invention may be chosen from the couplers conventionally used in oxidation dyeing and among which there may be mentioned in particular meta-phenylenediamines, meta-aminophenols, meta-diphenols and heterocyclic couplers such as for example indole derivatives, indoline derivatives, pyridine derivatives and pyrazolones, and their addition salts with an acid.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and their addition salts with an acid.

When they are present, these couplers preferably represent from 0.0001 to 10% by weight approximately of the total weight of the dyeing composition and still more preferably from 0.005 to 5% by weight approximately of this weight.

In general, the addition salts with an acid which can be used in the context of the invention (oxidation bases and couplers) are in particular chosen from the hydrochlorides, hydrobromides, sulphates, citrates, succinates, tartrates, lactates and acetates.

The dyeing composition in accordance with the invention may also contain various adjuvants which are conventionally used in hair-dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, antioxidants, penetrating agents, sequestering agents, perfumes, buffers, dispersing agents, conditioning agents such as for example silicones, film-forming agents, preservatives and opacifying agents.

Of course, persons skilled in the art will be careful to choose this or these possible additional compounds such that the advantageous properties intrinsically attached to the oxidation dyeing composition in accordance with the invention are not, or not substantially, impaired by the addition(s) envisaged.

The dyeing composition according to the invention may be provided in various forms, such as in the form of liquids, creams, gels or in any other form appropriate for carrying out a dyeing of keratinous fibres, and in particular human hair.

The subject of the invention is also a method of dyeing keratinous fibres, and in particular human keratinous fibres such as hair, using the dyeing composition as defined above.

The subject of the invention is also a method of oxidation dyeing of keratinous fibres, and in particular human keratinous fibres such as hair, using the dyeing composition as defined above.

According to this method, at least one dyeing composition as defined above is applied to the fibres for a period sufficient to develop the desired colour, either with air or with the aid of an oxidizing agent. The dyeing composition may optionally contain oxidation catalysts, in order to accelerate the oxidation process.

According to a first embodiment of the method of the invention, the dyeing of the fibres may be carried out without addition of an oxidizing agent, solely by contact with atmospheric oxygen.

According to second embodiment of the method of the invention, and in particular when the dyeing composition in accordance with the invention contains one or more oxidation bases and/or one or more couplers, at least one dyeing composition as defined above is applied to the fibres, the colour being developed at acidic, neutral or alkaline pH with the aid of an oxidizing agent which is added to the dyeing composition just at the time of use or which is present in an oxidizing composition applied simultaneously or sequentially in a separate manner.

According to this second embodiment of the dyeing method of the invention, the dyeing composition described above is preferably mixed, at the time of use, with an oxidizing composition containing, in a medium appropriate for dyeing, at least one oxidizing agent present in a sufficient quantity to develop a colour. The mixture obtained is then applied to the keratinous fibres and allowed to act for 3 to 50 minutes approximately, preferably 5 to 30 minutes approximately, after which they are washed with shampoo, rinsed again and dried.

The oxidizing agent present in the oxidizing composition as defined above may be chosen from oxidizing agents conventionally used for the oxidation dyeing of keratinous fibres, and among which there may be mentioned hydrogen peroxide, urea peroxide, alkali metal bromates, persalts such as perborates and persulphates and enzymes such as peroxidases, laccases, tyrosinases and oxidoreductases among which there may be mentioned in particular pyranose oxidases, glucose oxidases, glycerol oxidases, lactate oxidases, pyruvate oxidases and uricases.

The pH of the oxidizing composition containing the oxidizing agent as defined above is such that after mixing with the dyeing composition, the pH of the resulting composition applied to the keratinous fibres preferably varies between 3 and 12 approximately, and still more preferably between 5 and 11. It is adjusted to the desired value by means of acidifying or alkalinizing agents normally used for dyeing keratinous fibres and as defined above.

The oxidizing composition as defined above may also contain various adjuvants conventionally used in hair-dyeing compositions and as defined above.

The composition which is finally applied to the keratinous fibres may be provided in various forms, such as in the form of liquids, creams, gels, or in any other form appropriate for dyeing keratinous fibres, and in particular human hair.

Another subject of the invention is a multi-compartment device or dyeing "kit" or any other multi-compartment packaging system in which a first compartment contains the dyeing composition as defined above and a second compartment contains the oxidizing composition as defined above. These devices may be equipped with a means which makes it possible to deliver the desired mixture onto the hair, such as the devices described in Patent FR-2,586,913 in the name of the Applicant.

The following examples are intended to illustrate the invention but with no limitation being implied as a result.

EXAMPLE OF PREPARATION

Example of Preparation 1

Synthesis of 3-[2-(6-Aminobenzo[1,3]dioxol-5-ylamino)ethyl]-1-(4-{3-[2-(6-aminobenzo[1,3]dioxol-5-ylamino)ethyl]-3H-imidazol-1-ium}-butyl)-3H-imidazol-1-ium Dichloride, Dihydrochloride, Monohydrate

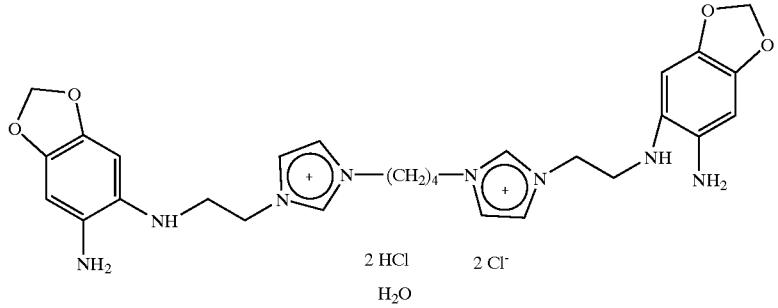

a) Preparation of (2-Chloroethyl)-(6-nitrobenzo[1,3]-dioxol-5-yl)amine

A solution of 100.0 g (0.44 mol) of 2-(6-nitrobenzo[1,3]dioxol-5-ylamino)ethanol (RN 106146-44-5) and 84 ml of triethylamine in 520 ml of dimethylformamide was made and cooled to a temperature of about 0° C.

40.8 ml (0.526 mol) of mesyl chloride were poured in dropwise over 40 minutes, and while the temperature was maintained between 0 and 5° C.

The temperature was allowed to rise to around 20° C. and 55.6 g (1.316 mol) of lithium chloride were added (the reaction was exothermic).

The mixture was heated for half an hour on a boiling water bath and poured into 1500 g of ice-cold water.

The crystallized precipitate was drained, made into a paste again in water and dried.

After recrystallization from ethyl acetate under reflux, 77.8 g of orange-coloured crystals of (2-chloroethyl)-(6-nitrobenzo[1,3]dioxol-5-yl)amine were obtained which melted at 120° C. (Kofler) and whose elemental analysis calculated for $C_9H_9N_2O_4Cl$ was:

| % | C | H | N | O | Cl |
|---|---|---|---|---|---|
| Calculated | 44.19 | 3.71 | 11.45 | 26.16 | 14.49 |
| Found | 44.31 | 3.70 | 11.68 | 26.40 | 14.30 | b) Preparation of 3-[2-(6-Nitrobenzo[1,3]dioxol-5-ylamino)ethyl]-1-(4-{3-[2-(6-nitrobenzo[1,3]dioxol-5-ylamino)ethyl]-3H-imidazol-1-ium}butyl)-3H-imidazol-1-ium Dichloride, Dihydrate.

A mixture of 48.9 g (0.2 mol) of (2-chloroethyl)-(6-nitrobenzo[1,3]dioxol-5-yl)amine and 20.3 g (0.1 mol) of 1,4-diimidazol-1-ylbutane (RN 69506-86-1) in 160 ml of isobutanol was heated under reflux for 18 hours.

It was cooled and the crystallized precipitate drained. After recrystallization from a mixture of 96% ethanol and water under reflux, 43.9 g of orange-coloured crystals of 3-[2-(6-nitrobenzo[1,3]dioxol-5-ylamino)-ethyl]-1-(4-{3-[2-(6-nitrobenzo[1,3]dioxol-5-ylamino)ethyl]-3H-imidazol-1-ium}butyl)-3H-imidazol-1-ium dichloride, dihydrate were obtained which melted at a temperature greater than 260° C. (Kofler) and whose elemental analysis calculated for $C_{28}H_{32}N_8O_8Cl_2+2H_2O$ was:

| % | C | H | N | O | Cl |
|---|---|---|---|---|---|
| Calculated | 47.00 | 5.07 | 15.66 | 22.36 | 9.91 |
| Found | 47.05 | 5.11 | 14.60 | 21.97 | 10.09 | c) Reduction of 3-[2-(6-Nitrobenzo[1,3]dioxol-5-ylamino)ethyl]-1-(4-{3-[2-(6-nitrobenzo[1,3]dioxol-5-ylamino)ethyl]-3H-imidazol-1-ium}butyl)-3H-imidazol-1-ium Dichloride, Dihydrate 30.0 g (0.042 mol) of the compound obtained above in the preceding step, 15 g of 5% palladium on carbon (containing 50% of water), 300 ml of 96% ethanol and 300 ml of water are placed in a hydrogenator.

The reduction is carried out over one hour at a hydrogen pressure of about 10 bar and at a temperature which was gradually increased to 70° C.

After filtration of the catalyst under nitrogen, the mixture was poured over 120 ml of 36% hydrochloric acid and the filtrate evaporated to dryness under reduced pressure.

The compound was taken up several times in absolute ethanol. After recrystallization from an ethanol/water mixture under reflux and drying at 40° C. under vacuum and over potassium hydroxide, 15.6 g of slightly grey crystals of 3-[2-(6-aminobenzo[1,3]-dioxol-5-ylamino)ethyl]-1-(4-{3-[2-(6-aminobenzo[1,3]dioxol-5-ylamino)ethyl]-3H-imidazol-1-ium}-butyl)-3H-imidazol-1-ium dichloride, dihydrochloride, monohydrate, were obtained which melted at a temperature greater than 260° C. (Kofler) and whose elemental analysis calculated for $C_{28}H_{38}N_8O_4Cl_4+H_2O$ was:

| % | C | H | N | O | Cl |
|---|---|---|---|---|---|
| Calculated | 47.34 | 5.67 | 15.77 | 11.26 | 19.96 |
| Found | 47.35 | 5.64 | 15.52 | 10.69 | 20.12 |

Examples of Application

Example 1 of Air Dyeing

The following dyeing composition in accordance with the invention was prepared at the time of use:

| | |
|---|---|
| 3-[2-(6-Aminobenzo[1,3]dioxol-5-ylamino)ethyl]-1-(4-{3-[2-(6-aminobenzo[1,3]-dioxol-5-ylamino)ethyl]-3H-imidazol-1-ium}butyl)-3H-imidazol-1-ium dichloride, dihydrochloride, monohydrate (compound of formula (I)) | 2.13 g |
| Ethanol at 96% | 20 g |
| Buffer pH $NH_4OH/NH_4Cl$ (1M/1M) | 10 g |
| Demineralized water qs | 100 g |

This composition was applied to locks of permanently waved grey hair which was 90% white, and the colour was allowed to develop for 30 minutes with no addition of oxidizing agent other than atmospheric oxygen.

The hair was then rinsed, washed with a standard shampoo, rinsed again and then dried.

The hair was dyed in a red-copper iridescent blond shade.

Example 2 of Dyeing in Neutral Medium

The following dyeing composition in accordance with the invention was prepared:

| | |
|---|---|
| 3-[2-(6-Aminobenzo[1,3]dioxol-5-ylamino)ethyl]-1-(4-{3-[2-(6-aminobenzo[1,3]-dioxol-5-ylamino)ethyl]-3H-imidazol-1-ium}butyl)-3H-imidazol-1-ium dichloride, dihydrochloride, monohydrate (compound of formula (I)) | 2.13 g |
| Ethanol at 96% | 18 g |
| Buffer $K_2HPO_4/KH_2PO_4$ (1.5M/1M) | 10 g |
| Sodium metabisulphite | 0.68 g |
| Pentasodium salt of diethylenetriaminopentaacetic acid | 1.1 g |
| Demineralized water qs | 100 g |

At the time of use, the above dyeing composition was mixed, weight for weight, with a solution of hydrogen peroxide at 20 volumes (6% by weight) of pH 3.

The mixture obtained was applied to locks of permanently waved grey hair which was 90% white for 30 minutes. The locks were then rinsed, washed with a standard shampoo, rinsed again and then dried.

The hair was dyed in a slightly golden iridescent dark blond shade.

Example 3 of Enzymatic Dyeing

The following ready-to-use dyeing composition was prepared:

| | |
|---|---|
| 3-[2-(6-Aminobenzo[1,3]dioxol-5-ylamino)ethyl]-1-(4-{3-[2-(6-aminobenzo[1,3]-dioxol-5-ylamino)ethyl]-3H-imidazol-1-ium}butyl)-3H-imidazol-1-ium dichloride, dihydrochloride, monohydrate (compound of formula (I)) | 2.13 g |
| Ethanol at 96% | 10 g |
| Uricase from Arthrobacter globiformis at 20 International Units (I.U.)/mg marketed by the company Sigma | 1.0 g |
| Uric acid | 1.0 g |
| Monoethanolamine qs | pH = 9.5 |
| Demineralized water qs | 100.0 g |

The ready-to-use dyeing composition described above was applied to locks of natural grey hair which was 90% white for 30 minutes. The hair was then rinsed, washed with a standard shampoo and then dried.

The hair was dyed in a coppery iridescent dark blond shade.

What is claimed is:

1. A compound of the following formula (I) an acid addition salt thereof:

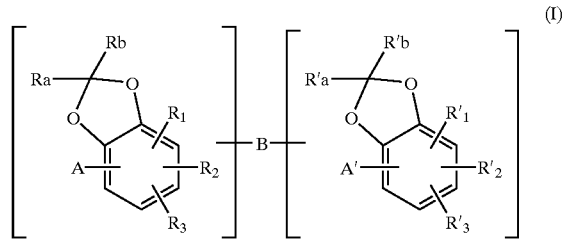

in which:

B is a linking arm chosen from linear and branched alkyl chains, which may be uninterrupted or interrupted by at least one group chosen from a group Z as defined below, an unsubstituted heteroatom, and a heteroatom substituted with at least one radical chosen from a hydroxyl radical and a $C_1$–$C_6$ alkoxy radical, said alkoxy radical being chosen from an alkoxy radical not carrying at least one ketone functional group and an alkoxy radical carrying at least one ketone functional group;

Ra, Rb, R'a and R'b, which are identical or different, are chosen from a hydrogen atom, a $C_1$–$C_6$ alkyl radical, a $C_1$–$C_6$ hydroxyalkyl radical, or formed in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, are chosen from a hydrogen atom; a halogen atom; one valence of the divalent linking arm B, a group Z as defined below; a group $A_2$ as defined below; a group $A_2'$ as defined a ($C_1$–$C_6$)alkylcarbonyl radical; an amino($C_1$–$C_6$)alkylcarbonyl radical; an N-Z-amino ($C_1$–$C_6$)alkylcarbonyl radical; an N-($C_1$–$C_6$) alkylamino($C_1$–$C_6$)alkylcarbonyl radical; an N,N-di ($C_1$–$C_6$ alkyl)amino($C_1$–$C_6$)alkylcarbonyl radical; an amino($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl ($C_1$–$C_6$)alkyl radical; an N,N-di($C_1$–$C_6$ alkyl)amino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N-Z-aminosulphonyl radical; an N-($C_1$–$C_6$ alkyl) aminosulphonyl radical; an N,N-di($C_1$–$C_6$alkyl) aminosulphonyl radical; an aminosulphonyl($C_1$–$C_6$) alkyl radical; an N-Z-aminosulphonyl($C_1$–$C_6$)alkyl radical; an N-($C_1$–$C_6$ alkyl)aminosulphonyl($C_1$–$C_6$) alkyl radical; an N,N-di($C_1$–$C_6$ alkyl)aminosulphonyl ($C_1$–$C_6$)alkyl radical; a carbamyl radical; an N-($C_1$–$C_6$ alkyl)carbamyl radical; an N,N-di($C_1$–$C_6$ alkyl) carbamyl radical; a carbamyl($C_1$–$C_6$)alkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$, $OR'_6$, $SR_6$ or $SR'_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two radicals, which are identical or different, chosen from an alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, an, N-($C_1$–$C_6$ alkyl)carbamyl, an N,N-di ($C_1$–$C_6$ alkyl)carbamyl radical, a, ($C_1$–$C_6$) alkylsulphonyl radical, a, formyl radical, a, trifluoro ($C_1$–$C_6$)alkylcarbonyl radical, a, ($C_1$–$C_6$) alkylcarboxyl, a thiocarbamyl radical, a group Z as defined below; and, formed together with the nitrogen atom to which they are attached, a 5- or 6-membered ring comprising at least one of atom chosen from a carbon atom and a heteroatom;

$R_6$ and $R'_6$, which may be identical or different, denote one valence of the divalent linking arm B; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a $C_1$–$C_6$ carboxyalkyl radical; a ($C_1$–$C_6$)alkylcarboxy($C_1$–$C_6$)alkyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$ alkyl)aminosulphonyl($C_1$–$C_6$)alkyl radical; an N,N-di($C_1$–$C_6$ alkyl)aminosulphonyl ($C_1$–$C_6$)alkyl radical; a ($C_1$–$C_6$)alkylsulphinyl($C_1$–$C_6$) alkylradical; a ($C_1$–$C_6$)alkylsulphonyl($C_1$–$C_6$)alkyl radical; a ($C_1$–$C_6$)alkylcarbonyl-($C_1$–$C_6$)alkyl radical; an amino($C_1$–$C_6$)alkyl radical; an amino($C_1$–$C_6$)alkyl radical in which the alkyl is unsubstituted or substituted with one or more hydroxyl radicals and in which the amine is substituted with one or two radicals, which are identical or different, chosen from a ($C_1$–$C_6$) alkylmonohydroxy($C_1$–$C_6$)alkyl radical, a, polyhydroxy($C_2$–$C_6$)alkyl radical, a, ($C_1$–$C_6$) alkylcarbonyl radical, a, formyl radical, a, trifluoro ($C_1$–$C_6$)alkylcarbonyl radical, a, ($C_1$–$C_6$)alkylcarboxyl radical, a, carbamyl radical, a, N-($C_1$–$C_6$ alkyl) carbamyl radical, a, N,N-di($C_1$–$C_6$ alkyl)carbamyl radical, a, thiocarbamyl radical, a ($C_1$–$C_6$) alkylsulphonyl radical, a group Z as defined below; and formed together with the nitrogen atom to which they are attached, a 5- or 6-membered ring comprising at least one atom chosen from a carbon atom and a heteroatom;

A is chosen from —$NR_4R_5$ and a hydroxyl radical;

A' is chosen from —$NR'_4R'_5$ and a hydroxyl radical;

$A_2$ is chosen from —$NR''_4R''_5$ and a hydroxyl radical;

$A'_2$ is chosen from —$NR'''_4R'''_5$ and a hydroxyl radical;

$R_4$, $R_5$, $R'_4$, $R'_5$, $R''_4$, $R''_5$, $R'''_4$ and $R'''_5$, which are identical or different, are chosen from one valence of the divalent linking arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a $C_1$–$C_6$ cyanoalkyl radical; a $C_1$–$C_6$ carbamylalkyl radical; an N-($C_1$–$C_6$ alkyl) carbamyl($C_1$–$C_6$)alkyl radical; an N,N-di($C_1$–$C_6$ alkyl) carbamyl($C_1$–$C_6$)alkyl radical; a $C_1$–$C_6$ thiocarbamylalkyl radical; a $C_1$–$C_6$ trifluoroalkyl radical; a $C_1$–$C_6$ sulphoalkyl radical; a ($C_1$–$C_6$)alkylcarboxy($C_1$–$C_6$) alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from a $C_1$–$C_6$ alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, a, N-($C_1$–$C_6$ alkyl)carbamyl radical, a, N,N-di($C_1$–$C_6$ alkyl)carbamyl radical, a, ($C_1$–$C_6$)alkylsulphonyl radical, a, formyl radical, a, trifluoro($C_1$–$C_6$alkyl) carbonyl radical, a, ($C_1$–$C_6$)alkylcarboxyl thiocarbamyl radical, a group Z as defined below; and formed together with the nitrogen atom to which they are attached a 5- or 6-membered ring comprising at least one atom chosen from a carbon atom and a heteroatom;

Z is chosen from the unsaturated cationic groups of the following formulae (II) and (III), and the saturated cationic groups of the following formula (IV):

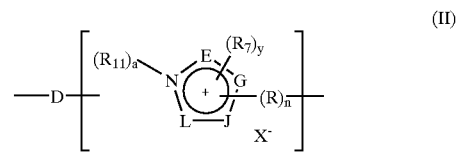

(II)

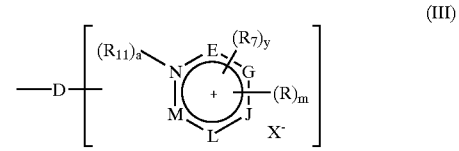

(III)

-continued

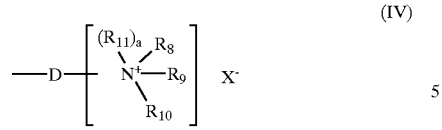

in which:
D is a linking arm chosen from a linear or branched alkyl chain, which may be interrupted by one or more heteroatoms, and which may be unsubstituted or substituted with at least one of radical chosen from a hydroxyl radical and a $C_1$–$C_6$ alkoxy radicals, and which may carry one or more ketone functions;
the members E, G, J, L and M, which are identical or different, are independently chosen from carbon, oxygen, sulphur and nitrogen atoms;
n is an integer between 0 and 4 inclusive;
m is an integer between 0 and 5 inclusive;
the radicals R, which are identical or different, are chosen from one valence of the divalent linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a tri($C_1$–$C_6$ alkyl)silane($C_1$–$C_6$)alkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$)alkylthio radical; an amino radical; an amino radical protected with a ($C_1$–$C_6$)alkylcarbonyl, carbamyl or ($C_1$–$C_6$) alkylsulphonyl radical; a group NHR", and a group NR"R'", in which R" and R'", which are identical or different, represent a $C_1$–$C_6$ alkyl radical, a $C_1$–$C_6$ monohydroxyalkyl radical or a $C_2$–$C_6$ polyhydroxyalkyl radical;
$R_7$ is chosen from a $C_1$–$C_6$ alkyl radical; one valence of the divalent linking arm B; a $C_1$–$C_6$ monohydroxyalkyl radical; a $C_2$–$C_6$ polyhydroxyalkyl radical; a $C_1$–$C_6$ cyanoalkyl radical; a tri($C_1$–$C_6$ alkyl)silane ($C_1$–$C_6$)alkyl radical; a ($C_1$–$C_6$)alkoxy($C_1$–$C_6$)alkyl radical; a $C_1$–$C_6$ carbamylalkyl radical; a ($C_1$–$C_6$) alkylcarboxy($C_1$–$C_6$)alkyl radical; a benzyl radical; and a second group Z which is identical or different from the first group Z;
$R_8$, $R_9$ and $R_{10}$, which are identical or different, are chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ cyanoalkyl radical; an aryl radical; a benzyl radical; a $C_1$–$C_6$ amidoalkyl radical; a tri($C_1$–$C_6$ alkyl)silane ($C_1$–$C_6$)alkyl radical; or a $C_1$–$C_6$ aminoalkyl radical in which the amine is protected by a ($C_1$–$C_6$) alkylcarbonyl, carbamyl or ($C_1$–$C_6$)alkylsulphonyl radical; two of the radicals $R_8$, $R_9$ and $R_{10}$ may also form together, with the nitrogen atom to which they are attached, a 5- or 6-membered saturated ring comprising at least one atom chosen from a carbon atom and a heteroatom, it being possible for the said ring to be unsubstituted or substituted with at least one of a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silane($C_1$–$C_6$)alkyl radical, an amido radical, an aldehydo radical, a carboxyl radical, a $C_1$–$C_6$ ketoalkyl radical, a thio radical, a $_1$–$C_6$ thioalkyl radical, a ($C_1$–$C_6$)alkylthio radical, and an amino radical, and an amino radical protected by a ($C_1$–$C_6$)alkylcarbonyl, carbamyl or ($C_1$–$C_6$)alkylsulphonyl radical;
one of the radicals $R_8$, $R_9$ and $R_{10}$ can be chosen from a second group Z which is identical to or different from the first group Z;
$R_{11}$ is chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or ($C_1$–$C_6$)alkylsulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silane($C_1$–$C_6$)alkyl radical; a $C_1$–$C_6$ sulphonamidoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$ alkyl) carbamyl($C_1$–$C_6$)alkyl radical; and an N-($C_1$–$C_6$ alkyl)sulphonamido($C_1$–$C_6$)alkyl radical;
a and y are integers equal to 0 or 1; with the following conditions:
in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively
2) when at least one of the members E, G, J and L represents a nitrogen atom to which the radical $R_7$ is attached;
in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;
in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring; and
$X^-$ is chosen from a monovalent anion and a divalent anion;
it being understood that:
the number of cationic groups Z is at least equal to 1.
2. A compound according to claim 1, characterized in that the rings of the unsaturated groups Z of formula (II) are chosen from pyrrole, imidazole, pyrazole, oxazole, thiazole and triazole rings.

3. A compound according to claim 1, characterized in that the rings of the unsaturated groups Z of formula (III) are chosen from pyridine, pyrimidine, pyrazine, oxazine and triazine rings.

4. A compound according to claim 1, characterized in that two of the radicals $R_8$, $R_9$ and $R_{10}$ form a ring chosen from pyrrolidine ring, a piperidine ring, a piperazine ring and morpholine ring, it being possible for said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silane($C_1$–$C_6$)alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$)alkylthio radical, an amino radical, an amino radical protected by a ($C_1$–$C_6$)alkylcarbonyl, carbamyl or ($C_1$–$C_6$)alkylsulphonyl radical.

5. A compound according to claim 1, characterized in that $X^-$ is chosen from halogen atom, a hydroxide, a hydrogen sulphate and a ($C_1$–$C_6$)alkylsulphate.

6. A compound according to claim 1 chosen from:

3-[2-(6-aminobenzo[1,3]dioxol-5-ylamino)ethyl]-1-(4-{3-[2-(6-aminobenzo[1,3]dioxol-5-ylamino)ethyl]-3H-imidazol-1-ium}butyl)-3H-imidazol-1-ium dichloride;

3-[2-(6-hydroxybenzo[1,3]dioxol-5-ylamino)ethyl]-1-(4-{3-[2-(6-hydroxybenzo[1,3]dioxol-5-ylamino)ethyl]-3H-imidazol-1-ium}butyl)-3H-imidazol-1-ium dichloride;

3-[2-(6-methoxybenzo[1,3]dioxol-5-ylamino)ethyl]-1-(4-{3-[2-(6-methoxybenzo[1,3]dioxol-5-ylamino)ethyl]-3H-imidazol-1-ium}butyl)-3H-imidazol-1-ium dichloride;

1,3-bis[3-(6-aminobenzo[1,3]dioxol-5-yloxy)propyl]-3H-imidazol-1-ium chloride;

3-[2-(6-aminobenzo[1,3]dioxol-5-yloxy)ethyl]-1-(4-{3-[2-(6-aminobenzo[1,3]dioxol-5-yloxy)ethyl]-3H-imidazol-1-ium}butyl)-3H-imidazol-1-ium dichloride;

3-[3-(6-aminobenzo[1,3]dioxol-5-yloxy)propyl]-1-(4-{3-[3-(6-aminobenzo[1,3]dioxol-5-yloxy)propyl]-3H-imidazol-1-ium}butyl)-3H-imidazol-1-ium dichloride;

3-[2-(6-aminobenzo[1,3]dioxol-5-yloxy)ethyl]-1-(3-{[2-(6-aminobenzo[1,3]dioxol-5-yloxy)ethyl]dimethylammonium}-propyl)-3H-imidazol-1-ium dichloride;

[2-(6-aminobenzo[1,3]dioxol-5-yloxy)ethyl]-(2-{[2-(6-aminobenzo[1,3]dioxol-5-yloxy)ethyl]dimethylammonium}ethyl)dimethylammonium dichloride;

and an acid addition salt of any of the foregoing.

7. A compound according to claim 1, characterized in that the acid addition salts are chosen from hydrochlorides, hydrobromides, sulphates, citrates, succinates, tartrates, lactates and acetates.

8. A method of oxidation dyeing of keratinous fibres, comprising using an oxidation dye precursor for the oxidation dyeing of keratinous fibres, wherein said oxidation dye precursor is chosen from at least one compound of the following formula (I) and acid addition salts thereof:

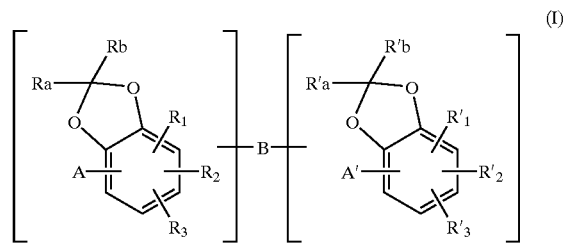

in which:

B is a linking arm chosen from linear and branched alkyl chains, which may be uninterrupted or interrupted by at least one group chosen from a group Z as defined below, an unsubstituted heteroatom, and a heteroatom substituted with at least one radical chosen from a hydroxyl radical and a $C_1$–$C_6$ alkoxy radical, said alkoxy radical being chosen from an alkoxy radical not carrying and an alkoxy radical carrying at least one ketone functional group;

Ra, Rb, R'a and R'b, which are identical or different, are chosen from a hydrogen atom, a $C_1$–$C_6$ alkyl radical, a $C_1$–$C_6$ hydroxyalkyl radical, or formed in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, are chosen from a hydrogen atom; a halogen atom; one valence of the divalent linking arm B, a group Z as defined below; a group $A_2$ as defined below; a group $A_2'$ as defined below; a ($C_1$–$C_6$) alkylcarbonyl radical; an amino($C_1$–$C_6$) alkylcarbonyl radical; an N-Z-amino($C_1$–$C_6$) alkylcarbonyl radical; an N-($C_1$–$C_6$)alkylamino($C_1$–$C_6$)alkylcarbonyl radical; an N,N-di($C_1$–$C_6$alkyl)amino($C_1$–$C_6$)alkylcarbonyl radical; an amino($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl($C_1$–$C_6$)alkyl radical; an N,N-di($C_1$–$C_6$ alkyl)amino($C_1$–$C_6$)alkylcarbonyl($C_1$–$C_6$)alkyl radical; a carboxyl radical; a ($C_1$–$C_6$)alkylcarboxyl radical; a ($C_1$–$C_6$)alkylsulphonyl radical; an aminosulphonyl radical; an N-Z-aminosulphonyl radical; an N-($C_1$–$C_6$ alkyl)aminosulphonyl radical; an N,N-di($C_1$–$C_6$alkyl)aminosulphonyl radical; an aminosulphonyl($C_1$–$C_6$)alkyl radical; an N-Z-aminosulphonyl($C_1$–$C_6$)alkyl radical; an N-($C_1$–$C_6$ alkyl)aminosulphonyl($C_1$–$C_6$)alkyl radical; an N,N-di($C_1$–$C_6$ alkyl)aminosulphonyl($C_1$–$C_6$)alkyl radical; a carbamyl radical; an N-($C_1$–$C_6$ alkyl)carbamyl radical; an N,N-di($C_1$–$C_6$ alkyl)carbamyl radical; a carbamyl($C_1$–$C_6$)alkyl radical; an N-($C_1$–$C_6$ alkyl) carbamyl($C_1$–$C_6$)alkyl radical; an N,N-di($C_1$–$C_6$ alkyl)carbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; a $C_1$–$C_6$ trifluoroalkyl radical; a cyano radical; a group $OR_6$, $OR'_6$, $SR_6$ or $SR'_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two radicals, which are identical or different, chosen from an alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, an, N-($C_1$–$C_6$ alkyl)carbamyl, an N,N-di($C_1$–$C_6$ alkyl)carbamyl radical, a, ($C_1$–$C_6$) alkylsulphonyl radical, a, formyl radical, a, trifluoro ($C_1$–$C_6$)alkylcarbonyl radical, a, ($C_1$–$C_6$) alkylcarboxyl, a thiocarbamyl radical, a group Z as defined below; and, formed together with the nitrogen atom to which they are attached, a 5- or 6-membered ring comprising at least one of atom chosen from a carbon atom and a heteroatom;

$R_6$ and $R'_6$, which may be identical or different, denote one valence of the divalent linking arm B; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a $C_1$–$C_6$ carboxyalkyl radical; a ($C_1$–$C_6$)alkylcarboxy($C_1$–$C_6$) alkyl radical; a $C_1$–$C_6$ cyanoalkyl radical; a $C_1$–$C_6$ carbamylalkyl radical; an N-($C_1$–$C_6$ alkyl)carbamyl ($C_1$–$C_6$)alkyl radical; an N,N-di($C_1$–$C_6$ alkyl) carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$ alkyl)aminosulphonyl($C_1$–$C_6$)alkyl radical; an N,N-di($C_1$–$C_6$ alkyl)aminosulphonyl($C_1$–$C_6$) alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an amino($C_1$–$C_6$)alkyl radical; an amino($C_1$–$C_6$)alkyl radical in which the alkyl is unsubstituted or substituted with one or more hydroxyl radicals and in which the amine is substituted with one or two radicals, which are identical or different, chosen from a ($C_1$–$C_6$)alkylmonohydroxy($C_1$–$C_6$)alkyl radical, a, polyhydroxy($C_2$–$C_6$)alkyl radical, a, ($C_1$–$C_6$)alkylcarbonyl radical, a, formyl radical, a, trifluoro($C_1$–$C_6$)alkylcarbonyl radical, a, ($C_1$–$C_6$) alkylcarboxyl radical, a, carbamyl radical, a, N-($C_1$–$C_6$ alkyl)carbamyl radical, a, N,N-di($C_1$–$C_6$ alkyl)carbamyl radical, a, thiocarbamyl radical, a ($C_1$–$C_6$)alkylsulphonyl radical, a group Z as defined below; and formed together with the nitrogen atom to which they are attached, a 5- or 6-membered ring comprising at least one atom chosen from a carbon atom and a heteroatom;

A is chosen from —$NR_4R_5$ and a hydroxyl radical;
A' is chosen from —$NR'_4R'_5$ and a hydroxyl radical;
$A_2$ is chosen from —$NR''_4R''_5$ and a hydroxyl radical;
$A'_2$ is chosen from —$NR'''_4R'''_5$ and a hydroxyl radical;
$R_4$, $R_5$, $R'_4$, $R'_5$, $R''_4$, $R''_5$, $R'''_4$ and $R'''_5$, which are identical or different, are chosen from one valence of the divalent linking arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di ($C_1$–$C_6$ alkyl)carbamyl($C_1$–$C_6$)alkyl radical; a $C_1$–$C_6$ thiocarbamylalkyl radical; a $C_1$–$C_6$ trifluoroalkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from a $C_1$–$C_6$ alkyl radical, a, $C_1$–$C_6$ monohydroxyalkyl radical, a, $C_2$–$C_6$ polyhydroxyalkyl radical, a, ($C_1$–$C_6$) alkylcarbonyl radical, a, carbamyl radical, a, N-($C_1$–$C_6$ alkyl)carbamyl radical, a, N,N-di($C_1$–$C_6$ alkyl)carbamyl radical, a, ($C_1$–$C_6$)alkylsulphonyl radical, a, formyl radical, a, trifluoro($C_1$–$C_6$ alkyl) carbonyl radical, a, ($C_1$–$C_6$)alkylcarboxyl thiocarbamyl radical, a group Z as defined below; and formed together with the nitrogen atom to which they are attached a 5- or 6-membered ring comprising at least one atom chosen from a carbon atom and a heteroatom;

Z is chosen from the unsaturated cationic groups of the following formulae (II) and (III), and the saturated cationic groups of the following formula (IV):

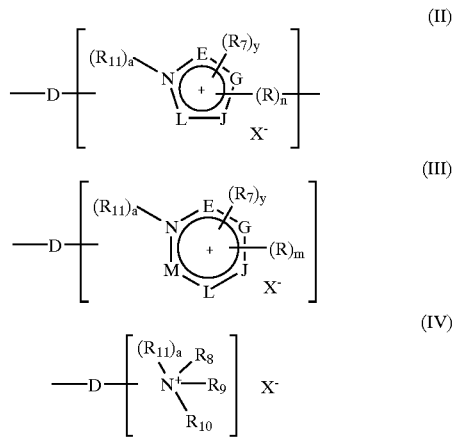

in which:

D is a linking arm chosen from a linear or branched alkyl chain, which may be interrupted by one or more heteroatoms, and which may be unsubstituted or substituted with at least one of radical chosen from a hydroxyl radical and a $C_1$–$C_6$ alkoxy radicals, and which may carry one or more ketone functions;

the members E, G, J, L and M, which are identical or different, are independently chosen from carbon, oxygen, sulphur and nitrogen atoms;

n is an integer between 0 and 4 inclusive;

m is an integer between 0 and 5 inclusive;

the radicals R, which are identical or different, are chosen from one valence of the divalent linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a tri($C_1$–$C_6$ alkyl)silane($C_1$–$C_6$)alkyl radical; an amido radical; an aldehydo radical; a carboxyl radical; a $C_1$–$C_6$ alkylcarbonyl radical; a thio radical; a $C_1-C_6$ thioalkyl radical; a $(C_1-C_6)$ alkylthio radical; an amino radical; an amino radical protected with a $(C_1-C_6)$alkylcarbonyl, carbamyl or $(C_1-C_6)$alkylsulphonyl radical; a group NHR", and a group NR"R'", in which R" and R'", which are identical or different, represent a $C_1-C_6$ alkyl radical, a $C_1-C_6$ monohydroxyalkyl radical or a $C_2-C_6$ polyhydroxyalkyl radical;

$R_7$ is chosen from a $C_1-C_6$ alkyl radical; one valence of the divalent linking arm B; a $C_1-C_6$ monohydroxyalkyl radical; a $C_2-C_6$ polyhydroxyalkyl radical; a $C_1-C_6$ cyanoalkyl radical; a tri($C_1-C_6$ alkyl)silane($C_1-C_6$)alkyl radical; a $(C_1-C_6)$alkoxy $(C_1-C_6)$alkyl radical; a $C_1-C_6$ carbamylalkyl radical; a $(C_1-C_6)$alkylcarboxy($C_1-C_6$)alkyl radical; a benzyl radical; and a second group Z which is identical or different from the first group Z;

$R_8$, $R_9$ and $R_{10}$, which are identical or different, are chosen from one valence of the divalent linking arm B; a $C_1-C_6$ alkyl radical; a $C_1-C_6$ monohydroxyalkyl radical; a $C_2-C_6$ polyhydroxyalkyl radical; a $(C_1-C_6)$alkoxy($C_1-C_6$)alkyl radical; a $C_1-C_6$ cyanoalkyl radical; an aryl radical; a benzyl radical; a $C_1-C_6$ amidoalkyl radical; a tri($C_1-C_6$ alkyl)silane($C_1-C_6$)alkyl radical; or a $C_1-C_6$ aminoalkyl radical in which the amine is protected by a $(C_1-C_6)$alkylcarbonyl, carbamyl or $(C_1-C_6)$ alkylsulphonyl radical; two of the radicals $R_8$, $R_9$ and $R_{10}$ may also form together, with the nitrogen atom to which they are attached, a 5- or 6-membered saturated ring comprising at least one atom chosen from a carbon atom and a heteroatom, it being possible for the said ring to be unsubstituted or substituted with at least one of a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a $C_1-C_6$ cyanoalkyl radical, a $C_1-C_6$ alkoxy radical, a tri($C_1-C_6$ alkyl)silane $(C_1-C_6)$alkyl radical, an amido radical, an aldehydo radical, a carboxyl radical, a $C_1-C_6$ ketoalkyl radical, a thio radical, a $C_1-C_6$ thioalkyl radical, a $(C_1-C_6)$alkylthio radical, and an amino radical, and an amino radical protected by a $(C_1-C_6)$alkylcarbonyl, carbamyl or $(C_1-C_6)$ alkylsulphonyl radical;

one of the radicals $R_8$, $R_9$ and $R_{10}$ can be chosen from a second group Z which is identical to or different from the first group Z;

$R_{11}$ is chosen from one valence of the divalent linking arm B; a $C_1-C_6$ alkyl radical; a $C_1-C_6$ monohydroxyalkyl radical; a $C_2-C_6$ polyhydroxyalkyl radical; an aryl radical; a benzyl radical; a $C_1-C_6$ aminoalkyl radical, a $C_1-C_6$ aminoalkyl radical in which the amine is protected with a $(C_1-C_6)$alkylcarbonyl, carbamyl or $(C_1-C_6)$ alkylsulphonyl radical; a $C_1-C_6$ carboxyalkyl radical; a $C_1-C_6$ cyanoalkyl radical; a $C_1-C_6$ carbamylalkyl radical; a $C_1-C_6$ trifluoroalkyl radical; a tri($C_1-C_6$ alkyl)silane($C_1-C_6$)alkyl radical; a $C_1-C_6$ sulphonamidoalkyl radical; a $(C_1-C_6)$ alkylcarboxy($C_1-C_6$)alkyl radical; a $(C_1-C_6)$ alkylsulphinyl($C_1-C_6$)alkyl radical; a $(C_1-C_6)$ alkylsulphonyl($C_1-C_6$)alkyl radical; a $(C_1-C_6)$ alkylketo($C_1-C_6$)alkyl radical; an N-($C_1-C_6$ alkyl)carbamyl($C_1-C_6$)alkyl radical; and an N-($C_1-C_6$ alkyl)sulphonamido($C_1-C_6$)alkyl radical;

a and y are integers equal to 0 or 1; with the following conditions:
in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively
2) when at least one of the members E, G, J and L represents a nitrogen atom to which the radical $R_7$ is attached;
in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;
in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring; and $X^-$ is chosen from a monovalent anion and a divalent anion;

it being understood that:
the number of cationic groups Z is at least equal to 1.

9. A composition for the oxidation dyeing of keratinous fibres, characterized in that it comprises, an oxidation dye precursor, in a medium appropriate for dyeing, wherein said oxidation dye precursor is chosen from at least one compound of the following formula (I) and acid addition salts thereof:

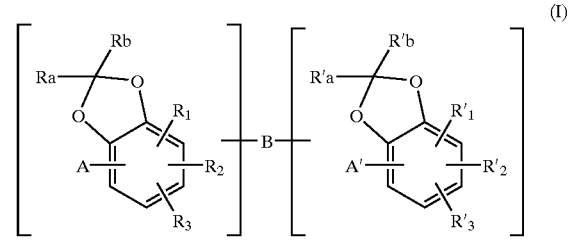

(I)

in which:
B is a linking arm chosen from linear and branched alkyl chains, which may be uninterrupted or interrupted by at least one group chosen from a group Z as defined below, an unsubstituted heteroatom, and a heteroatom substituted with at least one radical chosen from a hydroxyl radical and a $C_1-C_6$ alkoxy radical, said alkoxy radical being chosen from an alkoxy radical not carrying and an alkoxy radical carrying at least one ketone functional group;

Ra, Rb, R'a and R'b, which are identical or different, are chosen from a hydrogen atom, a $C_1$–$C_6$ alkyl radical, a $C_1$–$C_6$ hydroxyalkyl radical, or formed in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, are chosen from a hydrogen atom; a halogen atom; one valence of the divalent linking arm B, a group Z as defined below; a group $A_2$ as defined below; a group $A_2'$ as defined below; a ($C_1$–$C_6$)alkylcarbonyl radical; an amino($C_1$–$C_6$)alkylcarbonyl radical; an N-Z-amino($C_1$–$C_6$)alkylcarbonyl radical; an N-($C_1$–$C_6$)alkylamino($C_1$–$C_6$)alkylcarbonyl radical; an N,N-di($C_1$–$C_6$alkyl)amino($C_1$–$C_6$)alkylcarbonyl radical; an amino($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl ($C_1$–$C_6$)alkyl radical; an N,N-di($C_1$–$C_6$ alkyl)amino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N-Z-aminosulphonyl radical; an N-($C_1$–$C_6$ alkyl) aminosulphonyl radical; an N,N-di($C_1$–$C_6$alkyl) aminosulphonyl radical; an aminosulphonyl($C_1$–$C_6$) alkyl radical; an N-Z-aminosulphonyl($C_1$–$C_6$)alkyl radical; an N-($C_1$–$C_6$ alkyl)aminosulphonyl($C_1$–$C_6$) alkyl radical; an N,N-di($C_1$–$C_6$ alkyl)aminosulphonyl ($C_1$–$C_6$)alkyl radical; a carbamyl radical; an N-($C_1$–$C_6$ alkyl)carbamyl radical; an N,N-di($C_1$–$C_6$ alkyl) carbamyl radical; a carbamyl($C_1$–$C_6$)alkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$, $OR'_6$, $SR_6$ or $SR'_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two radicals, which are identical or different, chosen from an alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, an, N-($C_1$–$C_6$ alkyl)carbamyl, an N,N-di ($C_1$–$C_6$ alkyl)carbamyl radical, a, ($C_1$–$C_6$) alkylsulphonyl radical, a, formyl radical, a, trifluoro ($C_1$–$C_6$)alkylcarbonyl radical, a, ($C_1$–$C_6$) alkylcarboxyl, a thiocarbamyl radical, a group Z as defined below; and, formed together with the nitrogen atom to which they are attached, a 5- or 6-membered ring comprising at least one of atom chosen from a carbon atom and a heteroatom;

$R_6$ and $R'_6$, which may be identical or different, denote one valence of the divalent linking arm B; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a $C_1$–$C_6$ carboxyalkyl radical; a ($C_1$–$C_6$)alkylcarboxy($C_1$–$C_6$)alkyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di($C_1$–$C_6$ alkyl)carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$ alkyl)aminosulphonyl($C_1$–$C_6$)alkyl radical; an N,N-di($C_1$–$C_6$ alkyl)aminosulphonyl ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an amino($C_1$–$C_6$)alkyl radical; an amino($C_1$–$C_6$)alkyl radical in which the alkyl is unsubstituted or substituted with one or more hydroxyl radicals and in which the amine is substituted with one or two radicals, which are identical or different, chosen from a ($C_1$–$C_6$) alkylmonohydroxy($C_1$–$C_6$)alkyl radical, a, polyhydroxy($C_2$–$C_6$)alkyl radical, a, ($C_1$–$C_6$) alkylcarbonyl radical, a, formyl radical, a, trifluoro ($C_1$–$C_6$)alkylcarbonyl radical, a, ($C_1$–$C_6$)alkylcarboxyl radical, a, carbamyl radical, a, N-($C_1$–$C_6$ alkyl) carbamyl radical, a, N,N-di($C_1$–$C_6$ alkyl)carbamyl radical, a, thiocarbamyl radical, a ($C_1$–$C_6$) alkylsulphonyl radical, a group Z as defined below; and formed together with the nitrogen atom to which they are attached, a 5- or 6-membered ring comprising at least one atom chosen from a carbon atom and a heteroatom;

A is chosen from —$NR_4R_5$ and a hydroxyl radical;

A' is chosen from —$NR'_4R'_5$ and a hydroxyl radical;

$A_2$ is chosen from —$NR''_4R''_5$ and a hydroxyl radical;

$A'_2$ is chosen from —$NR'''_4R'''_5$ and a hydroxyl radical;

$R_4$, $R_5$, $R'_4$, $R'_5$, $R''_4$, $R''_5$, $R'''_4$ and $R'''_5$, which are identical or different, are chosen from one valence of the divalent linking arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a $C_1$–$C_6$ cyanoalkyl radical; a $C_1$–$C_6$ carbamylalkyl radical; an N-($C_1$–$C_6$ alkyl) carbamyl($C_1$–$C_6$)alkyl radical; an N,N-di($C_1$–$C_6$ alkyl) carbamyl($C_1$–$C_6$)alkyl radical; a $C_1$–$C_6$ thiocarbamylalkyl radical; a $C_1$–$C_6$ trifluoroalkyl radical; a $C_1$–$C_6$ sulphoalkyl radical; a ($C_1$–$C_6$)alkylcarboxy($C_1$–$C_6$) alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from a $C_1$–$C_6$ alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, a, N-($C_1$–$C_6$ alkyl)carbamyl radical, a, N,N-di($C_1$–$C_6$ alkyl)carbamyl radical, a, ($C_1$–$C_6$)alkylsulphonyl radical, a, formyl radical, a, trifluoro($C_1$–$C_6$ alkyl) carbonyl radical, a, ($C_1$–$C_6$)alkylcarboxyl thiocarbamyl radical, a group Z as defined below; and formed together with the nitrogen atom to which they are attached a 5- or 6-membered ring comprising at least one atom chosen from a carbon atom and a heteroatom;

Z is chosen from the unsaturated cationic groups of the following formulae (II) and (III), and the saturated cationic groups of the following formula (IV):

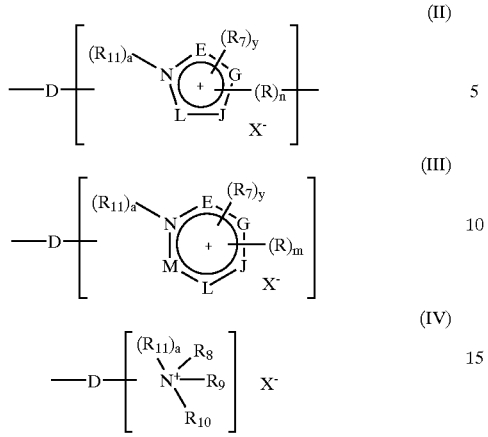

in which:
D is a linking arm chosen from a linear or branched alkyl chain, which may be interrupted by one or more heteroatoms, and which may be unsubstituted or substituted with at least one of radical chosen from a hydroxyl radical and a $C_1$–$C_6$ alkoxy radicals, and which may carry one or more ketone functions;
the members E, G, J, L and M, which are identical or different, are independently chosen from carbon, oxygen, sulphur and nitrogen atoms;
n is an integer between 0 and 4 inclusive;
m is an integer between 0 and 5 inclusive;
the radicals R, which are identical or different, are chosen from one valence of the divalent linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a tri($C_1$–$C_6$ alkyl)silane($C_1$–$C_6$)alkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$)alkylthio radical; an amino radical; an amino radical protected with a ($C_1$–$C_6$)alkylcarbonyl, carbamyl or ($C_1$–$C_6$) alkylsulphonyl radical; a group NHR", and a group NR"R'", in which R" and R'", which are identical or different, represent a $C_1$–$C_6$ alkyl radical, a $C_1$–$C_6$ monohydroxyalkyl radical or a $C_2$–$C_6$ polyhydroxyalkyl radical;
$R_7$ is chosen from a $C_1$–$C_6$ alkyl radical; one valence of the divalent linking arm B; a $C_1$–$C_6$ monohydroxyalkyl radical; a $C_2$–$C_6$ polyhydroxyalkyl radical; a $C_1$–$C_6$ cyanoalkyl radical; a tri($C_1$–$C_6$ alkyl)silane($C_1$–$C_6$)alkyl radical; a ($C_1$–$C_6$)alkoxy($C_1$–$C_6$)alkyl radical; a $C_1$–$C_6$ carbamylalkyl radical; a ($C_1$–$C_6$) alkylcarboxy($C_1$–$C_6$)alkyl radical; a benzyl radical; and a second group Z which is identical or different from the first group Z;
$R_8$, $R_9$ and $R_{10}$, which are identical or different, are chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ cyanoalkyl radical; an aryl radical; a benzyl radical; a $C_1$–$C_6$ amidoalkyl radical; a tri($C_1$–$C_6$ alkyl)silane ($C_1$–$C_6$)alkyl radical; or a $C_1$–$C_6$ aminoalkyl radical in which the amine is protected by a ($C_1$–$C_6$) alkylcarbonyl, carbamyl or ($C_1$–$C_6$)alkylsulphonyl radical; two of the radicals $R_8$, $R_9$ and $R_{10}$ may also form together, with the nitrogen atom to which they are attached, a 5- or 6-membered saturated ring comprising at least one atom chosen from a carbon atom and a heteroatom, it being possible for the said ring to be unsubstituted or substituted with at least one of a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silane($C_1$–$C_6$)alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$) alkylthio radical, and an amino radical, and an amino radical protected by a ($C_1$–$C_6$)alkylcarbonyl, carbamyl or ($C_1$–$C_6$)alkylsulphonyl radical;
one of the radicals $R_8$, $R_9$ and $R_{10}$ can be chosen from a second group Z which is identical to or different from the first group Z;
$R_{11}$ is chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or ($C_1$–$C_6$)alkylsulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silane($C_1$–$C_6$)alkyl radical; a $C_1$–$C_6$ sulphonamidoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$ alkyl) carbamyl($C_1$–$C_6$)alkyl radical; and an N-($C_1$–$C_6$ alkyl)sulphonamido($C_1$–$C_6$)alkyl radical;
a and y are integers equal to 0 or 1; with the following conditions:
in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively
2) when at least one of the members E, G, J and L represents a nitrogen atom to which the radical $R_7$ is attached;
in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;
in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring; and X⁻ is chosen from a monovalent anion and a divalent anion;

it being understood that:
  the number of cationic groups Z is at least equal to 1.

10. A composition according to claim 9, characterized in that the at least one compound of formula (I) represent from 0.0005 to 12% by weight of the total weight of the dyeing composition.

11. A composition according to claim 10, characterized in that the at least one compound of formula (I) represent from 0.005 to 6% by weight of the total weight of the dyeing composition.

12. A composition according to claim 9, characterized in that the composition comprises at least one oxidation base chosen from para-phenylenediamines, bisphenylalkylenediamines, para-aminophenols, ortho-aminophenols and heterocyclic bases.

13. A composition according to claim 12, characterized in that the heterocyclic bases are chosen from pyridine derivatives, pyrimidine derivatives and pyrazole derivatives.

14. A composition according to claim 12, characterized in that the at least one oxidation base represent from 0.0005 to 12% by weight of the total weight of the dyeing composition.

15. A composition according to claim 9, characterized in that the composition comprises
  at least one coupler chosen from meta-phenylenediamines, meta-aminophenols, meta-diphenols and heterocyclic couplers;
  at least one direct dye, and
  mixtures of any of the foregoing.

16. A composition according to claim 15, characterized in that the at least one coupler is chosen from 2-methyl-5-aminophenol, 5—N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and acid addition salts thereof.

17. A composition according to claim 15, characterized in that the at least one coupler represent from approximately 0.0001 to 10% by weight of the total weight of the dyeing composition.

18. A composition according to claim 9, characterized in that the acid addition salts are chosen from hydrochlorides, hydrobromides, sulphates, citrates, succinates, tartrates, lactates and acetates.

19. A method of oxidation dyeing of keratinous fibres, characterized in that at least one dyeing composition is applied to the fibres for a period sufficient to develop the desired color, either with air or with the aid of an oxidizing agent; wherein said at least one dyeing composition comprises an oxidation dye precursor, in a medium appropriate for dyeing, wherein said oxidation dye precursor is chosen from at least one compound of the following formula (I) and acid addition salts thereof:

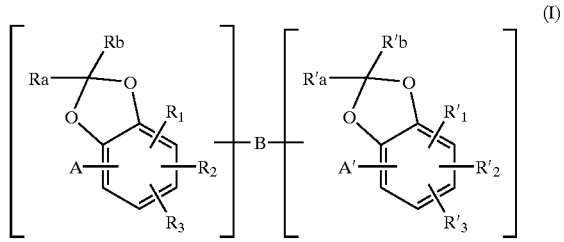

in which:

B is a linking arm chosen from linear and branched alkyl chains, which may be uninterrupted or interrupted by at least one group chosen from a group Z as defined below, an unsubstituted heteroatom, and a heteroatom substituted with at least one radical chosen from a hydroxyl radical and a $C_1$–$C_6$ alkoxy radical, said alkoxy radical being chosen from an alkoxy radical not carrying and an alkoxy radical carrying at least one ketone functional group;

Ra, Rb, R'a and R'b, which are identical or different, are chosen from a hydrogen atom, a $C_1$–$C_6$ alkyl radical, a $C_1$–$C_6$ hydroxyalkyl radical, or formed in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, are chosen from a hydrogen atom; a halogen atom; one valence of the divalent linking arm B, a group Z as defined below; a group $A_2$ as defined below; a group $A_2'$ as defined below; a ($C_1$–$C_6$) alkylcarbonyl radical; an amino($C_1$–$C_6$) alkylcarbonyl radical; an N-Z-amino($C_1$–$C_6$) alkylcarbonyl radical; an N-($C_1$–$C_6$)alkylamino ($C_1$–$C_6$)alkylcarbonyl radical; an N,N-di ($C_1$–$C_6$alkyl)amino($C_1$–$C_6$)alkylcarbonyl radical; an amino($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl ($C_1$–$C_6$)alkyl radical; an N,N-di($C_1$–$C_6$ alkyl)amino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$)alkylsulphonyl radical; an aminosulphonyl radical; an N-Z-aminosulphonyl radical; an N-($C_1$–$C_6$ alkyl)aminosulphonyl radical; an N,N-di ($C_1$–$C_6$ alkyl)aminosulphonyl radical; an aminosulphonyl($C_1$–$C_6$)alkyl radical; an N-Z-aminosulphonyl($C_1$–$C_6$)alkyl radical; an N-($C_1$–$C_6$ alkyl)aminosulphonyl($C_1$–$C_6$)alkyl radical; an N,N-di($C_1$–$C_6$ alkyl)aminosulphonyl($C_1$–$C_6$)alkyl radical; a carbamyl radical; an N-($C_1$–$C_6$ alkyl)carbamyl radical; an N,N-di($C_1$–$C_6$ alkyl)carbamyl radical; a carbamyl($C_1$–$C_6$)alkyl radical; an N-($C_1$–$C_6$ alkyl) carbamyl($C_1$–$C_6$)alkyl radical; an N,N-di($C_1$–$C_6$ alkyl)carbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; a $C_1$–$C_6$ trifluoroalkyl radical; a cyano radical; a group $OR_6$, $OR'_6$, $SR_6$ or $SR'_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two radicals, which are identical or different, chosen from an alkyl radical, a, $C_1$–$C_6$ monohydroxyalkyl radical, a, $C_2$–$C_6$ polyhydroxyalkyl radical, a, ($C_1$–$C_6$)alkylcarbonyl radical, a, carbamyl radical, an, N-($C_1$–$C_6$alkyl)carbamyl, an N,N-di($C_1$–$C_6$ alkyl)carbamyl radical, a, ($C_1$–$C_6$) alkylsulphonyl radical, a, formyl radical, a, trifluoro ($C_1$–$C_6$)alkylcarbonyl radical, a, ($C_1$–$C_6$) alkylcarboxyl, a thiocarbamyl radical, a group Z as defined below; and, formed together with the nitrogen atom to which they are attached, a 5- or 6-membered ring comprising at least one of atom chosen from a carbon atom and a heteroatom;

$R_6$ and $R'_6$, which may be identical or different, denote one valence of the divalent linking arm B; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a $C_1$–$C_6$ carboxyalkyl radical; a ($C_1$–$C_6$)alkylcarboxy($C_1$–$C_6$) alkyl radical; a $C_1$–$C_6$ cyanoalkyl radical; a $C_1$–$C_6$ carbamylalkyl radical; an N-($C_1$–$C_6$ alkyl)carbamyl ($C_1$–$C_6$)alkyl radical; an N,N-di($C_1$–$C_6$ alkyl) carbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$ alkyl)aminosulphonyl($C_1$–$C_6$)alkyl radical; an N,N-di($C_1$–$C_6$ alkyl)aminosulphonyl($C_1$–$C_6$) alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an amino($C_1$–$C_6$)alkyl radical; an amino($C_1$–$C_6$)alkyl radical in which the alkyl is unsubstituted or substituted with one or more hydroxyl radicals and in which the amine is substituted with one or two radicals, which are identical or different, chosen from a ($C_1$–$C_6$)alkylmonohydroxy($C_1$–$C_6$)alkyl radical, a, polyhydroxy($C_2$–$C_6$)alkyl radical, a, ($C_1$–$C_6$)alkylcarbonyl radical, a, formyl radical, a, trifluoro($C_1$–$C_6$)alkylcarbonyl radical, a, ($C_1$–$C_6$) alkylcarboxyl radical, a, carbamyl radical, a, N-($C_1$–$C_6$ alkyl)carbamyl radical, a, N,N-di($C_1$–$C_6$ alkyl)carbamyl radical, a, thiocarbamyl radical, a ($C_1$–$C_6$)alkylsulphonyl radical, a group Z as defined below; and formed together with the nitrogen atom to which they are attached, a 5- or 6-membered ring comprising at least one atom chosen from a carbon atom and a heteroatom;

A is chosen from —$NR_4R_5$ and a hydroxyl radical;
A' is chosen from —$NR'_4R'_5$ and a hydroxyl radical;
$A_2$ is chosen from —$NR''_4R''_5$ and a hydroxyl radical;
$A'_2$ is chosen from —$NR'''_4R'''_5$ and a hydroxyl radical;
$R_4$, $R_5$, $R'_4$, $R'_5$, $R''_4$, $R''_5$, $R'''_4$ and $R'''_5$, which are identical or different, are chosen from one valence of the divalent linking arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a $C_1$–$C_6$ cyanoalkyl radical; a $C_1$–$C_6$ carbamylalkyl radical; an N-($C_1$–$C_6$ alkyl)carbamyl($C_1$–$C_6$)alkyl radical; an N,N-di ($C_1$–$C_6$ alkyl)carbamyl($C_1$–$C_6$)alkyl radical; a $C_1$–$C_6$ thiocarbamylalkyl radical; a $C_1$–$C_6$ trifluoroalkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from a $C_1$–$C_6$ alkyl radical, a, $C_1$–$C_6$ monohydroxyalkyl radical, a, $C_2$–$C_6$ polyhydroxyalkyl radical, a, ($C_1$–$C_6$) alkylcarbonyl radical, a, carbamyl radical, a, N-($C_1$–$C_6$ alkyl)carbamyl radical, a, N,N-di($C_1$–$C_6$ alkyl)carbamyl radical, a, ($C_1$–$C_6$)alkylsulphonyl radical, a, formyl radical, a, trifluoro($C_1$–$C_6$ alkyl) carbonyl radical, a, ($C_1$–$C_6$)alkylcarboxyl thiocarbamyl radical, a group Z as defined below; and formed together with the nitrogen atom to which they are attached a 5- or 6-membered ring comprising at least one atom chosen from a carbon atom and a heteroatom;

Z is chosen from the unsaturated cationic groups of the following formulae (II) and (III), and the saturated cationic groups of the following formula (IV):

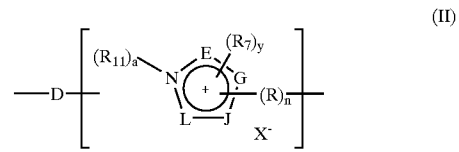

(II)

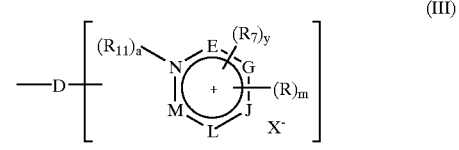

(III)

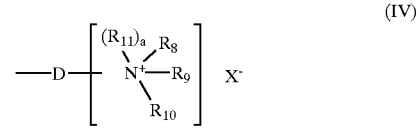

(IV)

in which:

D is a linking arm chosen from a linear or branched alkyl chain, which may be interrupted by one or more heteroatoms, and which may be unsubstituted or substituted with at least one of radical chosen from a hydroxyl radical and a $C_1$–$C_6$ alkoxy radicals, and which may carry one or more ketone functions;

the members E, G, J, L and M, which are identical or different, are independently chosen from carbon, oxygen, sulphur and nitrogen atoms;

n is an integer between 0 and 4 inclusive;

m is an integer between 0 and 5 inclusive;

the radicals R, which are identical or different, are chosen from one valence of the divalent linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical;

a tri($C_1$–$C_6$ alkyl)silane($C_1$–$C_6$)alkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$) alkylthio radical; an amino radical; an amino radical protected with a ($C_1$–$C_6$)alkylcarbonyl, carbamyl or ($C_1$–$C_6$)alkylsulphonyl radical; a group NHR", and a group NR"R"', in which R" and R"', which are identical or different, represent a $C_1$–$C_6$ alkyl radical, a $C_1$–$C_6$ monohydroxyalkyl radical or a $C_2$–$C_6$ polyhydroxyalkyl radical;

$R_7$ is chosen from a $C_1$–$C_6$ alkyl radical; one valence of the divalent linking arm B; a $C_1$–$C_6$ monohydroxyalkyl radical; a $C_2$–$C_6$ polyhydroxyalkyl radical; a $C_1$–$C_6$ cyanoalkyl radical; a tri($C_1$–$C_6$ alkyl)silane($C_1$–$C_6$)alkyl radical; a ($C_1$–$C_6$)alkoxy($C_1$–$C_6$)alkyl radical; a $C_1$–$C_6$ carbamylalkyl radical; a ($C_1$–$C_6$)alkylcarboxy($C_1$–$C_6$)alkyl radical; a benzyl radical; and a second group Z which is identical or different from the first group Z;

$R_8$, $R_9$ and $R_{10}$, which are identical or different, are chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ cyanoalkyl radical; an aryl radical; a benzyl radical; a $C_1$–$C_6$ amidoalkyl radical; a tri($C_1$–$C_6$ alkyl)silane($C_1$–$C_6$)alkyl radical; or a $C_1$–$C_6$ aminoalkyl radical in which the amine is protected by a ($C_1$–$C_6$)alkylcarbonyl, carbamyl or ($C_1$–$C_6$) alkylsulphonyl radical; two of the radicals $R_8$, $R_9$ and $R_{10}$ may also form together, with the nitrogen atom to which they are attached, a 5- or 6-membered saturated ring comprising at least one atom chosen from a carbon atom and a heteroatom, it being possible for the said ring to be unsubstituted or substituted with at least one of a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silane ($C_1$–$C_6$)alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$)alkylthio radical, and an amino radical, and an amino radical protected by a ($C_1$–$C_6$)alkylcarbonyl, carbamyl or ($C_1$–$C_6$) alkylsulphonyl radical;

one of the radicals $R_8$, $R_9$ and $R^{10}$ can be chosen from a second group Z which is identical to or different from the first group Z;

$R_{11}$ is chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or ($C_1$–$C_6$) alkylsulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silane($C_1$–$C_6$)alkyl radical; a $C_1$–$C_6$ sulphonamidoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$ alkyl)carbamyl($C_1$–$C_6$)alkyl radical; and an N-($C_1$–$C_6$ alkyl)sulphonamido($C_1$–$C_6$)alkyl radical;

a and y are integers equal to 0 or 1; with the following conditions:

in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively
2) when at least one of the members E, G, J and L represents a nitrogen atom to which the radical $R_7$ is attached;

in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;

in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring; and $X^-$ is chosen from a monovalent anion and a divalent anion;

it being understood that:
the number of cationic groups Z is at least equal to 1.

20. A method according to claim 19, characterized in that the fibres can be dyed without addition of an oxidizing agent, solely by contact with atmospheric oxygen.

21. A method according to claim 19, characterized in that the color is developed at at least one of an acidic, neutral, and an alkaline pH with the aid of an oxidizing agent which is added to the dyeing composition just at the time of use or which is present in an oxidizing composition applied simultaneously or sequentially in a separate manner.

22. A method according to claim 21, characterized in that the oxidizing agent is chosen from hydrogen peroxide, urea peroxide, alkali metal bromates, persalts and enzymes.

23. A method according to claim 22, characterized in that the enzymes are chosen from peroxidases, laccases, tyrosinases and oxidoreductases.

24. A method according to claim 23, characterized in that the oxidoreductases are chosen from pyranose oxidases, glucose oxidases, glycerol oxidases, lactate oxidases, pyruvate oxidases and uricases.

25. A multicompartment device or dyeing "kit" comprising first and second compartments, wherein the first compartment comprises a dyeing composition and a second compartment comprises an oxidizing composition, wherein the dyeing composition comprises an oxidation dye precursor, in a medium appropriate for dyeing, wherein said oxidation dye precursor is chosen from at least one compound of the following formula (I) and acid addition salts thereof:

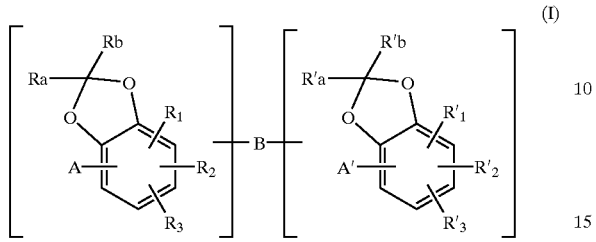

(I)

in which:

B is a linking arm chosen from linear and branched alkyl chains, which may be uninterrupted or interrupted by at least one group chosen from a group Z as defined below, an unsubstituted heteroatom, and a heteroatomsubstituted with at least one radical chosen from a hydroxyl radical and a $C_1-C_6$ alkoxy radical, said alkoxy radical being chosen from an alkoxy radical not carrying and an alkoxy radical carrying at least one ketone functional group;

Ra, Rb, R'a and R'b, which are identical or different, are chosen from a hydrogen atom, a $C_1-C_6$ alkyl radical, a $C_1-C_6$ hydroxyalkyl radical, or formed in pairs, together with the carbon atom to which they are attached, a 5-, 6- or 7-membered saturated carbon ring;

$R_1$, $R'_1$, $R_2$, $R'_2$, $R_3$ and $R'_3$, which may be identical or different, are chosen from a hydrogen atom; a halogen atom; one valence of the divalent linking arm B, a group Z as defined below; a group $A_2$ as defined below; a group $A_2'$ as defined below; a $(C_1-C_6)$alkylcarbonyl radical; an amino$(C_1-C_6)$alkylcarbonyl radical; an N-Z-amino$(C_1-C_6)$alkylcarbonyl radical; an N-$(C_1-C_6)$alkylamino$(C_1-C_6)$alkylcarbonyl radical; an N,N-di$(C_1-C_6$alkyl)amino$(C_1-C_6)$alkylcarbonyl radical; an amino$(C_1-C_6)$alkylcarbonyl$(C_1-C_6)$alkyl radical; an N-Z-amino$(C_1-C_6)$alkylcarbonyl$(C_1-C_6)$alkyl radical; an N-$(C_1-C_6)$alkylamino$(C_1-C_6)$alkylcarbonyl$(C_1-C_6)$alkyl radical; an N,N-di$(C_1-C_6$ alkyl)amino$(C_1-C_6)$alkylcarbonyl$(C_1-C_6)$alkyl radical; a carboxyl radical; a $(C_1-C_6)$alkylcarboxyl radical; a $(C_1-C_6)$alkylsulphonyl radical; an aminosulphonyl radical; an N-Z-aminosulphonyl radical; an N-$(C_1-C_6$ alkyl)aminosulphonyl radical; an N,N-di$(C_1-C_6$ alkyl)aminosulphonyl radical; an aminosulphonyl$(C_1-C_6)$alkyl radical; an N-Z-aminosulphonyl$(C_1-C_6)$alkyl radical; an N-$(C_1-C_6$ alkyl)aminosulphonyl$(C_1-C_6)$alkyl radical; an N,N-di$(C_1-C_6$ alkyl)aminosulphonyl$(C_1-C_6)$alkyl radical; a carbamyl radical; an N-$(C_1-C_6$ alkyl)carbamyl radical; an N,N-di$(C_1-C_6$ alkyl)carbamyl radical; a carbamyl$(C_1-C_6)$alkyl radical; an N-$(C_1-C_6$ alkyl) carbamyl$(C_1-C_6)$alkyl radical; an N,N-di$(C_1-C_6$ alkyl)carbamyl$(C_1-C_6)$alkyl radical; a $C_1-C_6$ alkyl radical; a $C_1-C_6$ monohydroxyalkyl radical; a $C_2-C_6$ polyhydroxyalkyl radical; a $(C_1-C_6)$alkoxy$(C_1-C_6)$ alkyl radical; a $C_1-C_6$ trifluoroalkyl radical; a cyano radical; a group $OR_6$, $OR'_6$, $SR_6$ or $SR'_6$; a $C_1-C_6$ aminoalkyl radical in which the alkyl is unsubstituted or substituted with one or more hydroxyl radicals; an amino$(C_1-C_6)$alkyl radical in which the alkyl is unsubstituted or substituted with one or more hydroxyl radicals and in which the amine is substituted with one or two radicals, which are identical or different, chosen from an alkyl radical, a, $C_1-C_6$ monohydroxyalkyl radical, a $C_2-C_6$ polyhydroxyalkyl radical, a, $(C_1-C_6)$alkylcarbonyl radical, a, carbamyl radical, an, N-$(C_1-C_6$ alkyl)carbamyl, an N,N-di$(C_1-C_6$ alkyl)carbamyl radical, a, $(C_1-C_6)$ alkylsulphonyl radical, a, formyl radical, a, trifluoro $(C_1-C_6)$alkylcarbonyl radical, a, $(C_1-C_6)$ alkylcarboxyl, a thiocarbamyl radical, a group Z as defined below; and, formed together with the nitrogen atom to which they are attached, a 5- or 6-membered ring comprising at least one of atom chosen from a carbon atom and a heteroatom;

$R_6$ and $R'_6$, which may be identical or different, denote one valence of the divalent linking arm B; a $C_1-C_6$ alkyl radical; a $C_1-C_6$ monohydroxyalkyl radical; a $C_2-C_6$ polyhydroxyalkyl radical; a group Z as defined below; a $(C_1-C_6)$alkoxy$(C_1-C_6)$alkyl radical; an aryl radical; a benzyl radical; a $C_1-C_6$ carboxyalkyl radical; a $(C_1-C_6)$alkylcarboxy$(C_1-C_6)$ alkyl radical; a $C_1-C_6$ cyanoalkyl radical; a $C_1-C_6$ carbamylalkyl radical; an N-$(C_1-C_6$ alkyl)carbamyl $(C_1-C_6)$alkyl radical; an N,N-di$(C_1-C_6$ alkyl) carbamyl$(C_1-C_6)$alkyl radical; a $C_1-C_6$ trifluoroalkyl radical; a $C_1-C_6$ aminosulphonylalkyl radical; a $C_1-C_6$ N-Z-aminosulphonylalkyl radical; an N-$(C_1-C_6$ alkyl)aminosulphonyl$(C_1-C_6)$alkyl radical; an N,N-di$(C_1-C_6$ alkyl)aminosulphonyl$(C_1-C_6)$ alkyl radical; a $(C_1-C_6)$alkylsulphinyl$(C_1-C_6)$alkyl radical; a $(C_1-C_6)$alkylsulphonyl$(C_1-C_6)$alkyl radical; a $(C_1-C_6)$alkylcarbonyl$(C_1-C_6)$alkyl radical; an amino$(C_1-C_6)$alkyl radical; an amino$(C_1-C_6)$alkyl radical in which the alkyl is unsubstituted or substituted with one or more hydroxyl radicals and in which the amine is substituted with one or two radicals, which are identical or different, chosen from a $(C_1-C_6)$alkylmonohydroxy$(C_1-C_6)$alkyl radical, a, polyhydroxy$(C_2-C_6)$alkyl radical, a, $(C_1-C_6)$alkylcarbonyl radical, a, formyl radical, a, trifluoro$(C_1-C_6)$alkylcarbonyl radical, a, $(C_1-C_6)$ alkylcarboxyl radical, a, carbamyl radical, a, N-$(C_1-C_6$ alkyl)carbamyl radical, a, N,N-di$(C_1-C_6$ alkyl)carbamyl radical, a, thiocarbamyl radical, a $(C_1-C_6)$alkylsulphonyl radical, a group Z as defined below; and formed together with the nitrogen atom to which they are attached, a 5- or 6-membered ring comprising at least one atom chosen from a carbon atom and a heteroatom;

A is chosen from $-NR_4R_5$ and a hydroxyl radical;

A' is chosen from $-NR'_4R'_5$ and a hydroxyl radical;

$A_2$ is chosen from $-NR''_4R''_5$ and a hydroxyl radical;

$A'_2$ is chosen from $-NR'''_4R'''_5$ and a hydroxyl radical;

$R_4$, $R_5$, $R'_4$, $R'_5$, $R''_4$, $R''_5$, $R'''_4$ and $R'''_5$, which are identical or different, are chosen from one valence of the divalent linking arm B; a hydrogen atom; a group Z as defined below; a $C_1-C_6$ alkyl radical; a $C_1-C_6$ monohydroxyalkyl radical; a $C_2-C_6$ polyhydroxyalkyl radical; a $(C_1-C_6)$alkoxy$(C_1-C_6)$alkyl radical; an aryl radical; a benzyl radical; a $C_1-C_6$ cyanoalkyl radical; a $C_1-C_6$ carbamylalkyl radical; an N-$(C_1-C_6$ alkyl)carbamyl$(C_1-C_6)$alkyl radical; an N,N-di $(C_1-C_6$ alkyl)carbamyl$(C_1-C_6)$alkyl radical; a $C_1-C_6$ thiocarbamylalkyl radical; a $C_1-C_6$ trifluoroalkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$ alkyl) aminosulphonyl($C_1$–$C_6$)alkyl radical; an N,N-di ($C_1$–$C_6$ alkyl)aminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two radicals, which are identical or different, chosen from a $C_1$–$C_6$ alkyl radical, a, $C_1$–$C_6$ monohydroxyalkyl radical, a, $C_2$–$C_6$ polyhydroxyalkyl radical, a, ($C_1$–$C_6$) alkylcarbonyl radical, a, carbamyl radical, a, N-($C_1$–$C_6$ alkyl)carbamyl radical, a, N,N-di($C_1$–$C_6$ alkyl)carbamyl radical, a, ($C_1$–$C_6$)alkylsulphonyl radical, a, formyl radical, a, trifluoro($C_1$–$C_6$ alkyl) carbonyl radical, a, ($C_1$–$C_6$)alkylcarboxyl thiocarbamyl radical, a group Z as defined below; and formed together with the nitrogen atom to which they are attached a 5- or 6-membered ring comprising at least one atom chosen from a carbon atom and a heteroatom;

Z is chosen from the unsaturated cationic groups of the following formulae (II) and (III), and the saturated cationic groups of the following formula (IV):

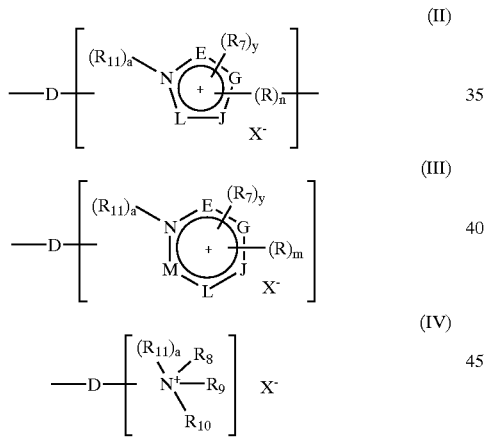

in which:

D is a linking arm chosen from a linear or branched alkyl chain, which may be interrupted by one or more heteroatoms, and which may be unsubstituted or substituted with at least one of radical chosen from a hydroxyl radical and a $C_1$–$C_6$ alkoxy radicals, and which may carry one or more ketone functions;

the members E, G, J, L and M, which are identical or different, are independently chosen from carbon, oxygen, sulphur and nitrogen atoms;

n is an integer between 0 and 4 inclusive;

m is an integer between 0 and 5 inclusive;

the radicals R, which are identical or different, are chosen from one valence of the divalent linking arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a tri($C_1$–$C_6$ alkyl)silane($C_1$–$C_6$)alkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$) alkylthio radical; an amino radical; an amino radical protected with a ($C_1$–$C_6$)alkylcarbonyl, carbamyl or ($C_1$–$C_6$)alkylsulphonyl radical; a group NHR″, and a group NR″R‴, in which R″ and R‴, which are identical or different, represent a $C_1$–$C_6$ alkyl radical, a $C_1$–$C_6$ monohydroxyalkyl radical or a $C_2$–$C_6$ polyhydroxyalkyl radical;

$R_7$ is chosen from a $C_1$–$C_6$ alkyl radical; one valence of the divalent linking arm B; a $C_1$–$C_6$ monohydroxyalkyl radical; a $C_2$–$C_6$ polyhydroxyalkyl radical; a $C_1$–$C_6$ cyanoalkyl radical; a tri($C_1$–$C_6$ alkyl)silane($C_1$–$C_6$)alkyl radical; a ($C_1$–$C_6$)alkoxy ($C_1$–$C_6$)alkyl radical; a $C_1$–$C_6$ carbamylalkyl radical; a ($C_1$–$C_6$)alkylcarboxy($C_1$–$C_6$)alkyl radical; a benzyl radical; and a second group Z which is identical or different from the first group Z;

$R_8$, $R_9$ and $R_{10}$, which are identical or different, are chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ cyanoalkyl radical; an aryl radical; a benzyl radical; a $C_1$–$C_6$ amidoalkyl radical; a tri($C_1$–$C_6$ alkyl)silane($C_1$–$C_6$)alkyl radical; or a $C_1$–$C_6$ aminoalkyl radical in which the amine is protected by a ($C_1$–$C_6$)alkylcarbonyl, carbamyl or ($C_1$–$C_6$)alkylsulphonyl radical; two of the radicals $R_8$, $R_9$ and $R_{10}$ may also form together, with the nitrogen atom to which they are attached, a 5- or 6-membered saturated ring comprising at least one atom chosen from a carbon atom and a heteroatom, it being possible for the said ring to be unsubstituted or substituted with at least one of a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silane($C_1$–$C_6$)alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$)alkylthio radical, and an amino radical, and an amino radical protected by a ($C_1$–$C_6$)alkylcarbonyl, carbamyl or ($C_1$–$C_6$)alkylsulphonyl radical;

one of the radicals $R_8$, $R_9$ and $R_{10}$ can be chosen from a second group Z which is identical to or different from the first group Z;

$R_{11}$ is chosen from one valence of the divalent linking arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or ($C_1$–$C_6$) alkylsulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silane($C_1$–$C_6$)alkyl radical; a $C_1$–$C_6$ sulphonamidoalkyl radical; a ($C_1$–$C_6$)

alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$ alkyl)carbamyl($C_1$–$C_6$)alkyl radical; and an N-($C_1$–$C_6$ alkyl)sulphonamido($C_1$–$C_6$)alkyl radical;

a and y are integers equal to 0 or 1; with the following conditions:

in the unsaturated cationic groups of formula (II):
when a=0, the linking arm D is attached to the nitrogen atom,
when a=1, the linking arm D is attached to one of the members E, G, J or L,
y can only take the value 1:
1) when the members E, G, J and L simultaneously represent a carbon atom and when the radical $R_7$ is carried by the nitrogen atom of the unsaturated ring; or alternatively
2) when at least one of the members E, G, J and L represents a nitrogen atom to which the radical $R_7$ is attached;

in the unsaturated cationic groups of formula (III):
when a=0, the linking arm D is attached to the nitrogen atom,
when a=1, the linking arm D is attached to one of the members E, G, J, L or M,
y can only take the value 1 when at least one of the members E, G, J, L and M represents a divalent atom, and when the radical $R_7$ is carried by the nitrogen atom of the unsaturated ring;

in the cationic groups of formula (IV):
when a=0, then the linking arm D is attached to the nitrogen atom carrying the radicals $R_8$ to $R_{10}$,
when a=1, then two of the radicals $R_8$ to $R_{10}$ form together with the nitrogen atom to which they are attached a 5- or 6-membered saturated ring as defined above, and the linking arm D is carried by a carbon atom of the said saturated ring; and $X^-$ is chosen from a monovalent anion and a divalent anion;

it being understood that:

the number of cationic groups Z is at least equal to 1.

26. The compound according to claim 1, wherein the linking arm B is chosen from linear and branched divalent alkyl groups comprising from 1 to 14 carbon atoms, which may be chosen from linking arms interrupted by at least one group chosen from groups Z, unsubstituted heteroatoms, and heteroatom substituted with at least one radical chosen from hydroxyl and $C_1$ to $C_6$ alkoxy radicals, said alkoxy radicals being chosen from alkoxy radicals not carrying and carrying at least one ketone functional group.

27. The compound according to claim 1, wherein the linking arm B is chosen from linear and branched alkyl chains interrupted by at least one heteroatom chosen from oxygen, sulphur, and nitrogen atoms.

28. The compound according to claim 1, wherein the linking arm D is chosen from linear and branched divalent alkyl groups comprising from 1 to 14 carbon atoms, which may be chosen from linking arms interrupted by at least one group chosen from groups Z, unsubstituted heteroatoms, and heteroatom substituted with at least one radical chosen from hydroxyl and $C_1$ to $C_6$ alkoxy radicals, said alkoxy radicals being chosen from alkoxy radicals not carrying and carrying at least one ketone functional group.

29. The compound according to claim 1, wherein the linking arm D is chosen from linear and branched alkyl chains interrupted by at least one heteroatom chosen from oxygen, sulphur, and nitrogen atoms.

30. The compounds according to claim 6, wherein the acid addition salts are chosen from hydrochlorides, hydrobromides, sulphates, citrates, succinates, tartrates, lactates and acetates.

31. The method according to claim 19, wherein said keratinous fibres are human keratinous fibres.

* * * * *

UNITED STATES PATENT AND TRADEMARK OFFICE
CERTIFICATE OF CORRECTION

PATENT NO.   : 6,402,791 B1
DATED        : June 11, 2002
INVENTOR(S)  : Alain Genet et al.

It is certified that error appears in the above-identified patent and that said Letters Patent is hereby corrected as shown below:

<u>Column 16,</u>
Line 64, after "defined" insert -- below; --.

Signed and Sealed this

Thirtieth Day of July, 2002

Attest:

Attesting Officer

JAMES E. ROGAN
*Director of the United States Patent and Trademark Office*